(12) United States Patent
Tiernan

(10) Patent No.: US 7,250,757 B1
(45) Date of Patent: Jul. 31, 2007

(54) APPARATUS AND METHOD FOR CIRCUIT ANALYSIS USING MAGNETIC AND ELECTROMAGNETIC STIMULATION OF THE CIRCUIT FOR DUAL MAGNETIC FIELD IMAGING

(75) Inventor: Tim Tiernan, Newton, MA (US)

(73) Assignee: Radiation Monitoring Devices, Inc., Watertown, MA (US)

( * ) Notice: Subject to any disclaimer, the term of this patent is extended or adjusted under 35 U.S.C. 154(b) by 0 days.

(21) Appl. No.: 11/120,510

(22) Filed: May 2, 2005

Related U.S. Application Data

(60) Provisional application No. 60/610,981, filed on Sep. 16, 2004.

(51) Int. Cl.
*G01N 27/82* (2006.01)
*G01N 27/72* (2006.01)

(52) U.S. Cl. .................... 324/238; 324/237; 324/228

(58) Field of Classification Search ............... None
See application file for complete search history.

(56) References Cited

U.S. PATENT DOCUMENTS

| | | | |
|---|---|---|---|
| 5,218,294 A | * | 6/1993 | Soiferman ............... 324/158.1 |
| 6,975,108 B2 | * | 12/2005 | Bilik et al. ............... 324/237 |
| 2003/0071615 A1 | * | 4/2003 | Schlicker et al. ......... 324/242 |

OTHER PUBLICATIONS

Kacprzak et al., Interpretation of Printed Circuit Boards Structures via Amplitude and signals phase Obtained from the ECT testings, 6th International workshop on Electromagnetic Non-Destructive Evaluation 2000.6.*

* cited by examiner

*Primary Examiner*—Jay M. Patidar
(74) *Attorney, Agent, or Firm*—Townsend and Townsend and Crew LLP

(57) ABSTRACT

A material analysis system configured to determine whether a circuit is defective includes a magnetic field generator configured to generate a first magnetic field that is configured to induce at least one eddy current in a conductive portion of the circuit, wherein the eddy current induces a second magnetic field; a set of magnetic field sensors configured to detect the second magnetic field and generate a set of image information therefrom; a database that includes circuit information for the circuit; and a computing device configured to receive the image information from the set of magnetic field sensors and retrieve the circuit information from the database, wherein the computing device is configured to compare the image information to the circuit information to determine whether the circuit is defective.

27 Claims, 23 Drawing Sheets
(7 of 23 Drawing Sheet(s) Filed in Color)

Magneto Resistive Sensors And
Electrical Contacts On Silicon

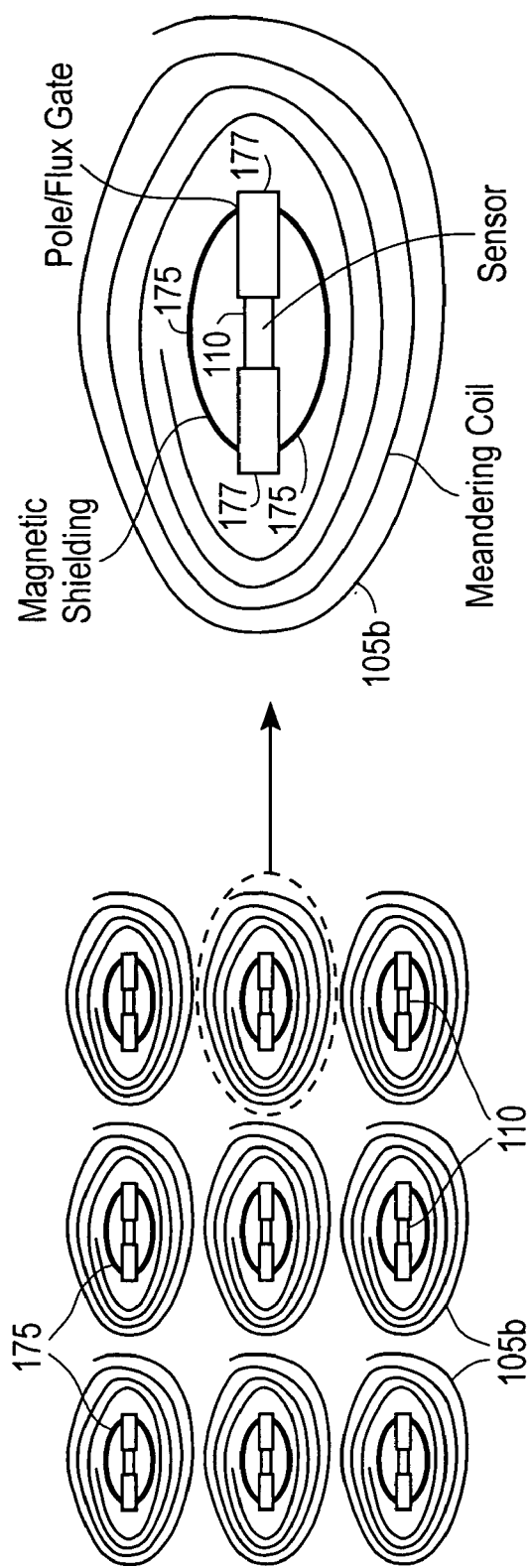

Sensors Fabricated On A Conformal Substrate
(Such As Polyimide On A Gel Polymer)
To Make Intimate Contact With A Contoured Surface High Density "Bed Of Nails" Arrangement With Sensors On Each Nail.
A 2-D Array Of Sensors Conforms To The PCB And Component Shapes
(Only A Few Sensors Shown For Clarity)

Circuit Under Inspection

Magnetic Field Image Of A Broken Trace On A PCB

Operating Cycles Of A Circuit And Correlated Phase Positions Associated With Images Generated At The Phase Positions Component Having Hidden Defects May Be Analyzed And Mapped One Voxel At A Time 385a → (left image) Trace 1, 2nd Layer To 3rd Layer. Trace 2, Bottom Layer To 3rd Layer. The Right Image Shows No Current Due To An Open In The Trace. Trace 3, 2nd Layer To 1st Layer. ← 385b No Opens, Three Traces.

Figure 4 Magnetic Images Of A Multi-layer PCB. Left Side Is Normal. Right Side Has An Open Circuit On Trace 2.

Trace 2 Is Open. Only 2 Traces, Center Trace Open.

Magnified Image Of Hot Zone Showing Relatively
High Current Confined To An Area Of
Approximately 12.5 Microns × 125 Microns Magnetic Images Of A Capacitor

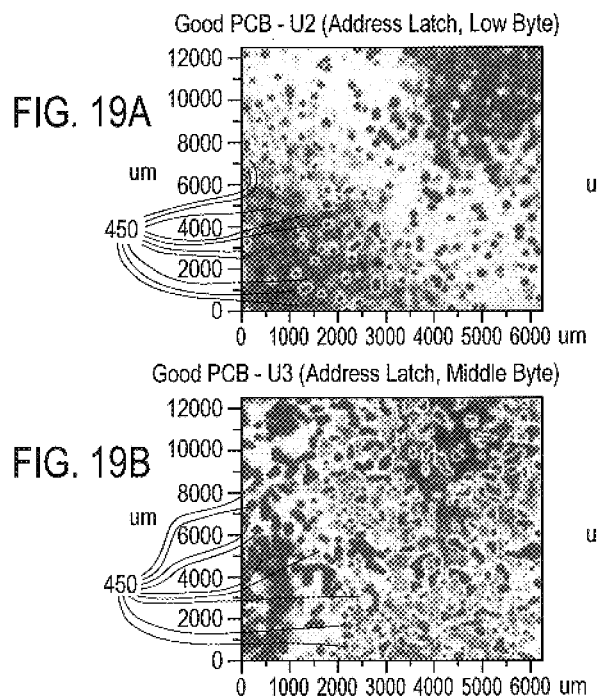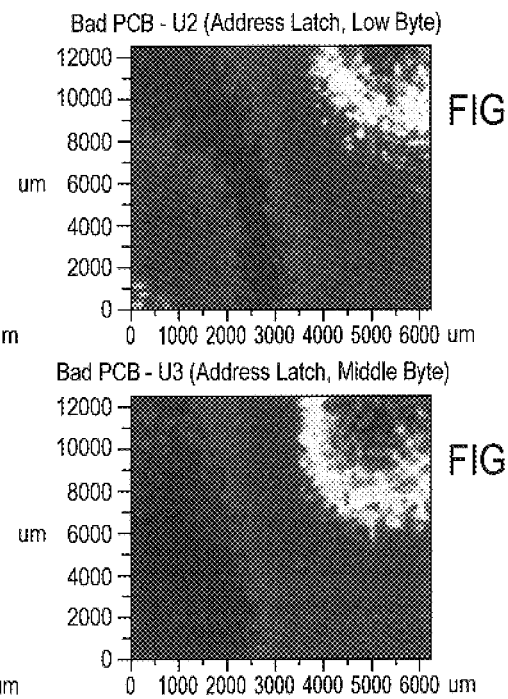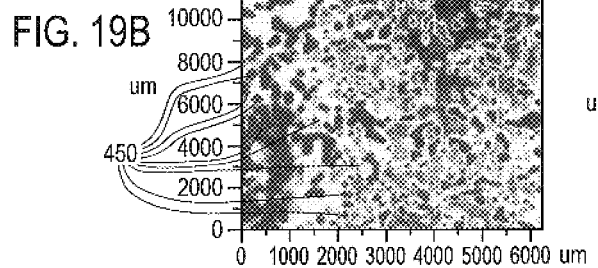
FIG. 19A  Good PCB - U2 (Address Latch, Low Byte)
FIG. 19B  Good PCB - U3 (Address Latch, Middle Byte)
FIG. 19C  Bad PCB - U2 (Address Latch, Low Byte)
FIG. 19D  Bad PCB - U3 (Address Latch, Middle Byte)

Magnetic Field Images Of Bi-directional Transceivers

Magnetic Images Of Two Relays

APPARATUS AND METHOD FOR CIRCUIT ANALYSIS USING MAGNETIC AND ELECTROMAGNETIC STIMULATION OF THE CIRCUIT FOR DUAL MAGNETIC FIELD IMAGING

CROSS-REFERENCES TO RELATED APPLICATIONS

This application claims priority to U.S. Provisional Patent Application No. 60/610,981, filed Sep. 16, 2004, titled "Printed Circuit Board and Integrated Circuit Analysis Device and Methods Utilizing Dual Mode Magnetic Field Imaging Microscopy" of Tim Tiernan, the disclosure of which is incorporated by reference herein in its entirety for all purposes.

BACKGROUND OF THE INVENTION

The present invention relates generally to circuit analysis, and more specifically relates to generating images of circuits via dual-mode magnetic field induction for defect analysis.

The testing and analysis of circuits, printed circuit boards (PCBs) and the like is a complex and a costly step in the manufacture of these devices. Moreover, the complexity and the cost of circuit test and analysis continues to rise as circuits and PCBs are continually made smaller. As used hereinafter, the term "circuit" refers to circuits, PCBs, PCBs having attached circuits and the like unless otherwise indicated. The rise in the complexity and the cost of testing and analysis of circuits is attributable, in part, to the tester interfaces used to contact circuits for passing electrical test signals to the circuits and receiving response signals therefrom. Traditional tester interfaces include bed of nails interfaces, sockets, probe cards and the like. As the pitch of circuit interface contacts (e.g., contact pads, bonding pads, solder balls, solder mounds, leads, and the like) enter the sub-millimeter range, the micron range, and the sub-micron range, the pitch of adjacent tester contacts on tester interfaces similarly enter these ranges. The costs associated with the manufacture of such tester interfaces and the maintenance fees therefore, rise to relatively high levels yielding testing and analysis of circuits relatively costly.

Testing and analysis of circuits are costly due not only to the relatively high cost for development, manufacture, and maintenance of tester interfaces, but also because for each unique circuit, a unique tester interface is typically manufactured for the circuit. Moreover, unique test programs are typically generated to drive each unique circuit and its associated tester interface. Test program development typically takes a few days to several months and even a year or more for relatively complex circuits.

Further, contact testing of circuits often fails to expose flaws that lead to relatively early failure (often referred to as infant mortality) of circuits. For example, contact testing is often of limited use for detecting flaws in metal lines (e.g., cracks, voids, etc.) and circuit elements (e.g., transistors, inductors, resistors, etc.) that are operational, but that have defects that may lead to uneven heating and the like, which in turn often leads to relatively high infant mortality. Flaws that lead to high infant mortality are often detected through destructive techniques that ultimately render devices unsuitable for their intended use.

Therefore, new apparatus and methods are needed that provide for limited physical contact with circuits under test, have a relatively low dedication to specific circuits, and that are configured to non-destructively detect internal flaws that may not be detected via contact testing techniques.

BRIEF SUMMARY OF THE INVENTION

The present invention provides a material analysis system configured to determine whether a circuit is defective. The system includes a magnetic field generator configured to generate a first magnetic field that is configured to induce at least one eddy current in a conductive portion of the circuit, wherein the eddy current induces a second magnetic field. A set of magnetic field sensors of the system is configured to detect the second magnetic field and generate a set of image information therefrom. A database of the system includes circuit information for the circuit. A computing device of the system is configured to receive the image information from the set of magnetic field sensors and retrieve the circuit information from the database, wherein the computing device is configured to compare the image information to the circuit information to determine whether the circuit is defective. According to a specific embodiment, the set of magnetic field generators includes a SQUID magnetometer, a set of Fluxgates, a set of Hall effect sensors, a set of magnetostrictive materials, and/or a set of magneto-resistive elements. The image information includes an image of the circuit and/or magnetic amplitude information for the second magnetic field; and the circuit information includes a test image, a circuit layout, an image of a fabrication mask, a design specification, a design layout, and/or a conductor map. According to a further specific embodiment, the system includes an electrical stimulation device configured to electrically stimulate the circuit, wherein a current associated with the electrical stimulus is configured to generate a third magnetic field in the conductive portion of the circuit, wherein the set of magnetic field sensors is configured to detect the third magnetic field and generate a second set of image information therefrom, and the computing device is configured to receive the second set of image information from the set of magnetic field sensors and compare the second set of image information to the circuit information to determine whether the circuit is defective.

According to another embodiment, a method is provided for determining whether a circuit is defective. The method includes generating a first magnetic field that is configured to induce at least one eddy current in a conductive portion of the circuit, wherein the eddy current induces a second magnetic field; detecting the second magnetic field; generating a set of image information from the detected second magnetic field; comparing the image information to predefined circuit information for the circuit; and determining whether the circuit is defective based on the comparison. The method might further include storing the predetermined circuit information in a database; and retrieving the predetermined circuit information from the database prior to the comparison step. The image information includes an image of the circuit, the predetermined circuit information includes a predetermined image for the circuit, and the comparing step includes comparing the image for the circuit and the predetermined image for the circuit. The predetermined image includes a predetermined image of a non-defective circuit and/or a defective circuit having a known defect. According to a specific embodiment, the method further includes displaying the image of the circuit and the predetermined image of the circuit and a display. The step of displaying may include superimposing the image of the circuit and the predetermined image of the circuit. According to another specific embodiment, the method further includes, electrically stimulating the circuit; generating a third magnetic field based on the electrical stimulus in the conductive portion of the circuit; detecting the third magnetic field; generating a second set of image information from the detected third magnetic field; comparing the second set of image information with the predetermined image information; and determining whether the circuit is defective based on the comparison.

A further understanding of the nature and advantages of the present invention may be realized by reference to the remaining portions of the specification and the drawings.

BRIEF DESCRIPTION OF THE DRAWINGS

The patent or application file contains at least one drawing executed in color. Copies of this patent or patent application publication with the color drawings will be provided by the Office upon request and payment of the necessary fee.

FIGS. 7A and 7B are simplified top views of one embodiment of a plurality of magnetic field generators according to one embodiment of the present invention;

FIGS. 19A–19D are simplified images of address latches of the CPU that might be generated by the material analysis system according to one embodiment of the present invention;

DETAILED DESCRIPTION OF THE INVENTION

The present invention provides an apparatus and method for generating images of circuits and printed circuit boards (PCBs), and more specifically provides dual mode magnetic imaging of circuits and PCBs wherein one or more magnetoresistive sensors are configured to detect magnetic fields induced in circuits and PCBs to generate images thereof. The generated images might be used for defect analysis of circuits and PCBs in the field, in development, in manufacturing and the like.

Apparatus Overview and Eddy Current Induction

Figure 1:
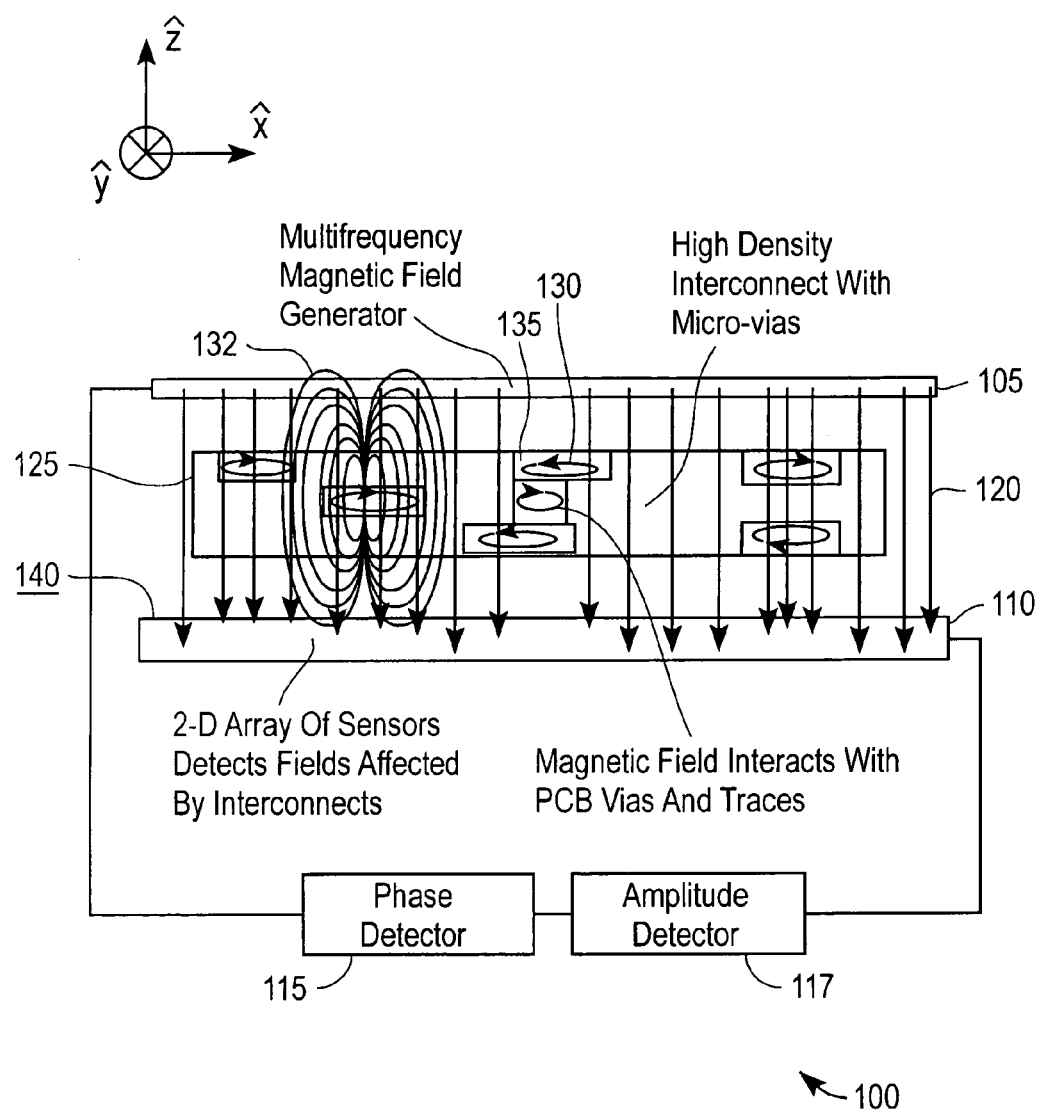
FIG. 1 is a simplified block diagram of a dual-mode magnetic imager according to one embodiment of the present invention.

FIG. 1 is a simplified block diagram of a dual-mode magnetic imager (DMMI) 100 according to one embodiment of the present invention. DMMI 100 includes a magnetic field generator 105, a set of magnetic field sensors 110, a phase detector 115, and an amplitude detector 117. A set, as referred to herein, includes one or more elements. Magnetic field generator 105 is configured to generate a magnetic field 120 in a material 125. Material 125 may include nearly any type of material that includes at least one conductive portion. For example, material 125 may include one or more circuits, one or more PCBs, a PCB to which one or more circuits are attached to form a more complex circuit and the like. For convenience and unless otherwise indicated, the term "circuit" as used herein refers to one or more circuits (e.g., integrated circuits), one or more PCBs, a PCB to which one or more circuits are attached and the like. The remainder of the description describes the specific embodiment in which material 125 is a circuit. It should be understood, however, the apparatus and methods described herein are applicable more generally to nearly any material 125 that includes at least one conductive portion.

Applied magnetic field 120 may be a static magnetic field and/or a dynamic magnetic field. For example, the field generator might be configured to generate a dynamic magnetic field that has varying intensity and/or varying direction that vary at a constant frequency (5 Hz, 10 Hz, 20 Hz, 50 Hz, etc.) and/or a varying frequency. Magnetic field 120 is configured to induce one or more eddy currents 130 in conductive portions 135 of circuit 125. The conductive portions of the circuit may include metal lines, metal pads, polysilicon, wire bonds, bond pads, doped semiconductors, etc. While the present description discusses the induction of eddy current in a circuit, the magnetic field generator may be configured to include eddy currents in nearly any material, device, etc. in which a current might be induced to flow via an applied magnetic field.

As described briefly above, magnetic field 120 is configured to magnetically induce one or more eddy currents 130 in the conductive portions of the circuit. The eddy currents 130 in turn generate one or more induced magnetic fields 132. Induced magnetic fields 132 generate a counter magnetomotive force that interacts with the magnetic field generator 105 and can alter the applied magnetic field 120, alter the impedance of the magnetic field generator (e.g., a coil magnetic field generator), and thereby tend to reduce the applied magnetic field strength. According to one embodiment, the magnetic field generator is driven by a constant current coil driver, which provides a substantially uniform output independent if the magnetic field generator is subject to the induced magnetic fields from the circuit.

The set of magnetic field sensors 110 is configured to detect magnetic field 120 generated by magnetic field generator 105 and induced magnetic fields 132 generated by eddy currents 130. The set of magnetic field sensors are further configured to generate electrical signals proportional to the amplitudes of the detected magnetic fields 120 and 132. Alternatively, the magnetic field sensors might be configured to detect only the induced magnetic field if, for example, the magnetic field detectors are magnetically shielded to substantially prevent detection of magnetic field 120. Magnetic shielding is described in detail below.

The set of magnetic field sensors 110 is currently described in further detail. According to one embodiment, the set of magnetic field sensors includes a set of SQUID magnetometers, a set of Fluxgates, a set of Hall effect sensors, a set of magnetostrictive materials, and/or a set of magneto-resistive elements that is configured to detect the magnetic fields generated by the magnetic field generator and the circuit. The particular embodiment in which the set of magnetic field sensors includes a set of magneto-resistive elements is presently described. It should be understood, that the particular described embodiment, is applicable to other embodiments in which the set of magnetic field sensors includes a set of SQUID magnetometers, a set of Fluxgates, a set of Hall effect sensors, a set of magnetostrictive materials or the like. As is known in the art, magneto resistors are configured to change electrical properties in the presence of a magnetic field. Specifically, the resistance of magneto-resistive elements changes in the presence of a magnetic field. The resistance change may be detected by placing a voltage (e.g., a constant voltage) across each magneto-resistive element and measuring a current flow change through the element, or driving a current (e.g., a constant current) through each element and measuring a voltage change across the element. The bias current may also be an AC current that is particularly useful for measuring the DC magnetic fields generated by conductors carrying DC signals. The AC bias allows the reduction of the 1/f noise common with DC sensor measurements. The magneto-resistive elements may include Giant magneto-resistive (GMR) sensors, anisotropic magneto-resistive (AMR) sensors, tunnel junction magneto-resistive sensors or the like. AMR sensors exhibit resistance changes in the presence of a magnetic field (e.g., magnetic field 120 and/or magnetic field 132) without the application of a biasing magnetic field, whereas GMR sensors exhibit resistance changes in the presence of a magnetic field if a biasing magnetic field is applied. In embodiments of the present invention that include GMR sensors, a biasing magnetic field generator (not shown) is configured to generate a biasing magnetic field that is applied to the GMR sensors.

Magneto-resistive sensors generally have a given axis that exhibits a relatively large resistance change if the detected magnetic field substantially aligns with this given axis. Other axes of magneto-resistive sensors also tend to exhibit resistance changes in the presence of a magnetic field, but this resistance change is generally smaller than the resistance change along the given axis. The given axis is generally set during manufacturing of magneto-resistive sensors by applying a magnetic field along the given axis as the magneto-resistive sensors are formed. According to one embodiment of the present invention, the given axis is oriented substantially parallel (e.g., parallel to the x-axis and y-axis) to surface 140 of magnetic field sensors 110, substantially perpendicular (e.g., along the z-axis) to surface 140 or otherwise advantageously oriented to substantially optimize magnetic field detection. The x, y, and z axes are indicated in FIG. 1. The x-axis is shown in FIG. 1 as horizontal to the page; the z-axis is vertical to the page; and the y-axis is perpendicular to the plane of the page and is designated by the customary symbol ⊗.

Figure 2:
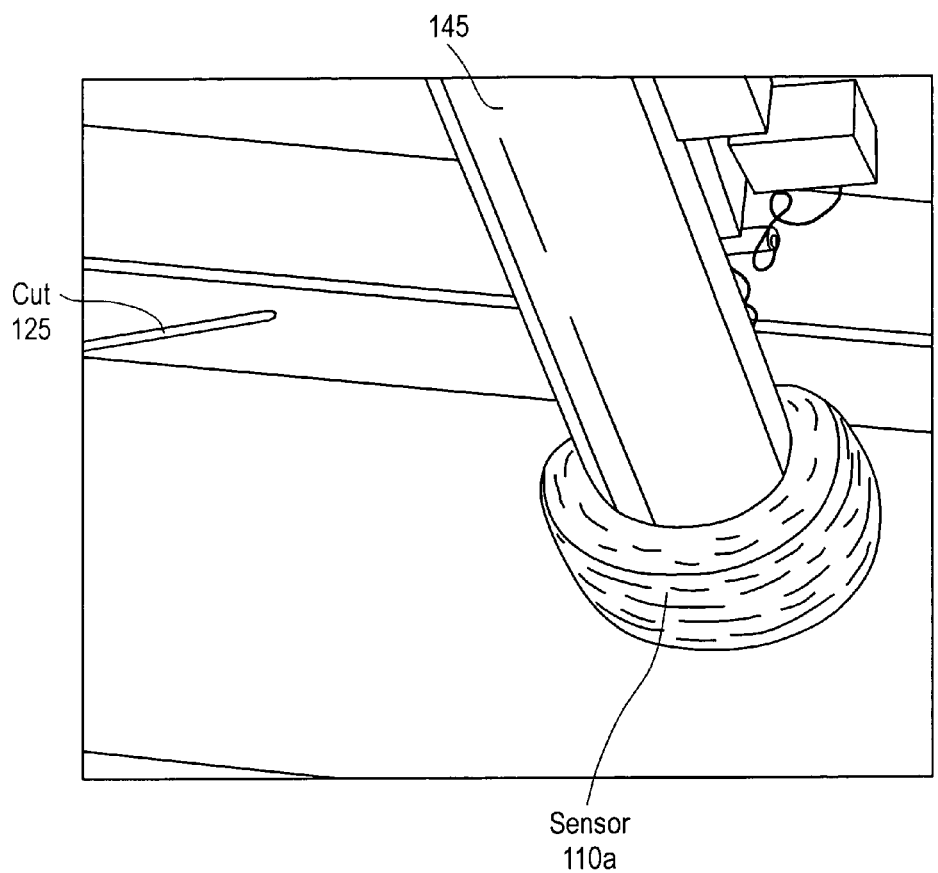
FIG. 2 is a perspective view of a magnetic field sensor that is disposed at substantially the end of a translation device that is configured to move the sensor across the surface of a circuit.

FIG. 2 is a perspective view of a sensor 110a that is disposed at substantially the end of a translation device 145 that is configured to move the sensor across the surface of circuit 125. It should be understood that while sensor 110a is described as being configured to be moved across the surface of circuit 125, circuit 125 might be configured to move by the translation device while sensor 110a remains stationary, or both the circuit and the sensor may be configured to move by one or more translation devices 145. Translation device 145 might include a number of devices configured to move the sensor. For example, translation device 145 may include one or more of a piezoelectric device, an electromechanical device (e.g., a solenoid), a mechanical device (e.g., micrometer screw) or the like. The translation device is configured to maintain the orientation (e.g., parallel) of the magnetic field sensors substantially constant relative to the surface of the circuit, and/or maintain the distance between the sensors and the surface of the circuit as substantially fixed. Various position sensors configured to maintain the orientation and the distance of the sensor to the surface of the circuit are described in detail below.

Figure 3:
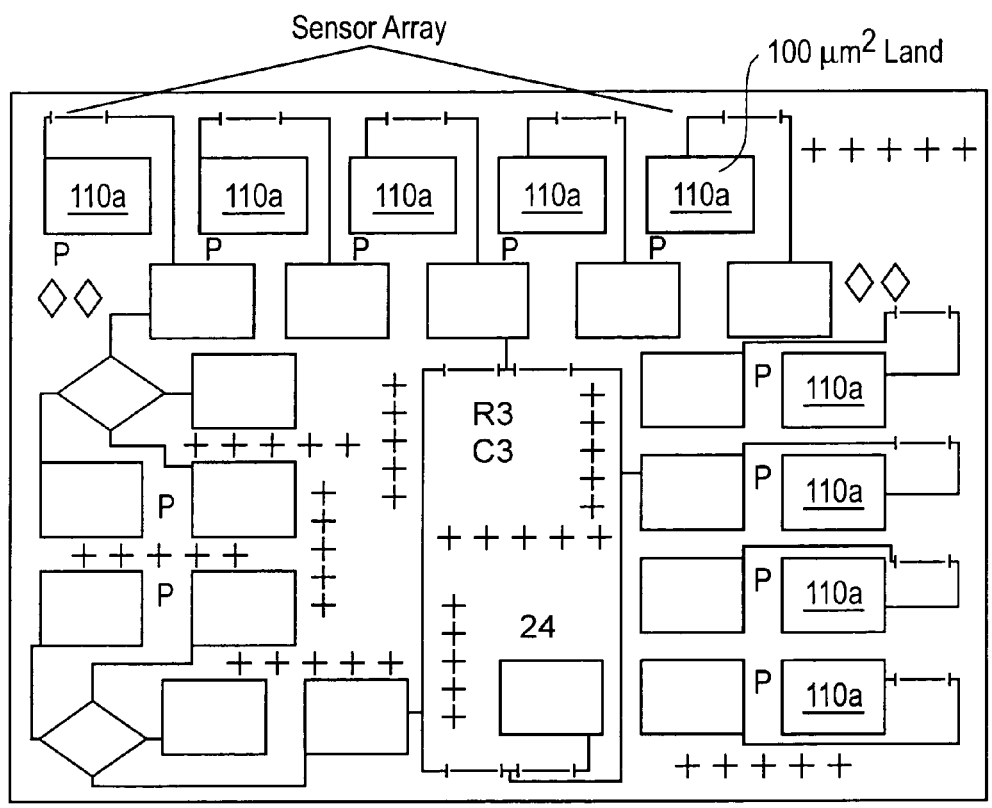
FIG. 3 is a simplified circuit diagram of a set of magnetic field sensors arranged two-dimensionally on an integrated circuit.

The set of magnetic field sensors (e.g., magneto-resistive sensors) may be arranged linearly, two-dimensionally (e.g., in a two-dimensional array), or three-dimensionally (e.g., in a three-dimensional array). FIG. 3 is a simplified circuit diagram of a set of magnetic field sensors 110 arranged two-dimensionally on a circuit 150 (e.g., integrated circuit). Circuit 150 might include additional circuitry for controlling the sensors. For example, circuit 150 might include circuitry for applying voltage across the sensors and detecting the current change associated with the sensor resistance change. For example, the circuit might be configured to control the application of voltage or current to each sensor individually so that one or more select sensors can be selectively activated for magnetic field detection. Circuit 150 might also include phase detector 115 and amplitude detector 117 or other circuits configured to analyze detected magnetic fields for generating images (also referred to herein sometimes as image frames) of circuit 125. Alternatively, the phase detector, the amplitude detector and the like may be disposed on circuits other than circuit 150 and may be locally disposed with respect to the sensors or remotely disposed in one or more computing devices (explained in further detail below). According to one embodiment, the magnetic field sensors that are disposed on circuit 150 have a length of about 100 microns to about 0.25 microns inclusive and a width of about 100 microns to about 0.25 microns inclusive. According to a specific embodiment, the sensors have a length of about 30 microns and a width of about 8 microns. According to the specific embodiment, the pitch of adjacent magnetic field sensors (e.g., center to center) is about 125 microns. According to one embodiment, each magnetic field sensor has a dynamic range of about 100 Orstead and a sensitivity of about 400 micro-volts per Orstead.

According to another embodiment, magnetic field generator 105 includes one or more electromagnets and/or one or more solid state magnets or combinations thereof. For example, magnetic field generator may include one or more metal coils, superconducting coils, ferromagnets or the like. Magnetic fields generated by the magnetic field generator may have field lines that are substantially parallel to circuit 125, substantially perpendicular to circuit 125 or otherwise advantageously aligned.

Figure 4A:
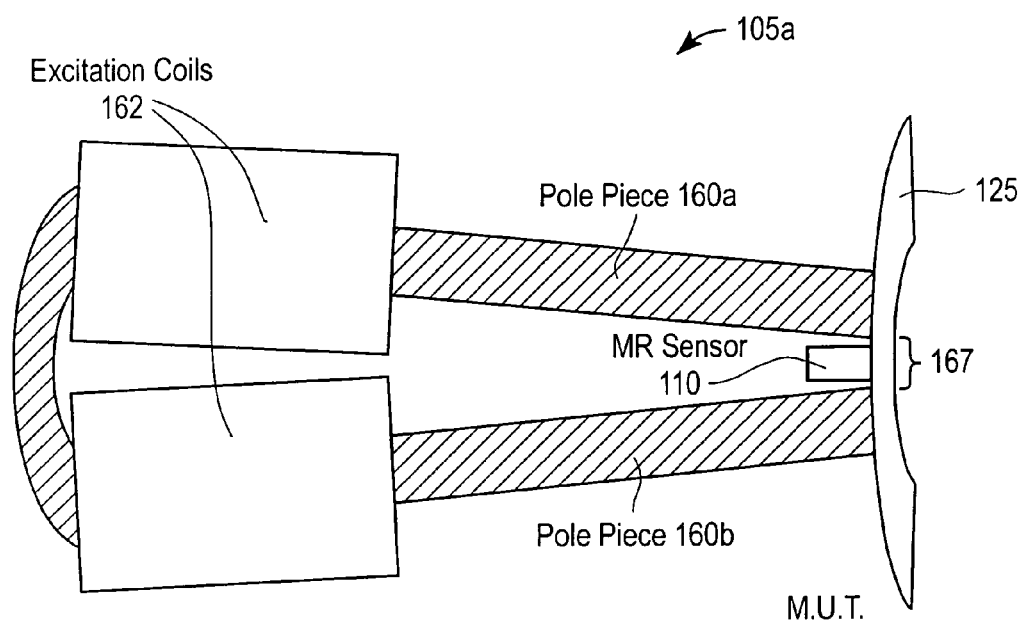
FIGS. 4A and 4B are simplified side views of a magnetic field generator according to one embodiment of the present invention.
Figure 4B:
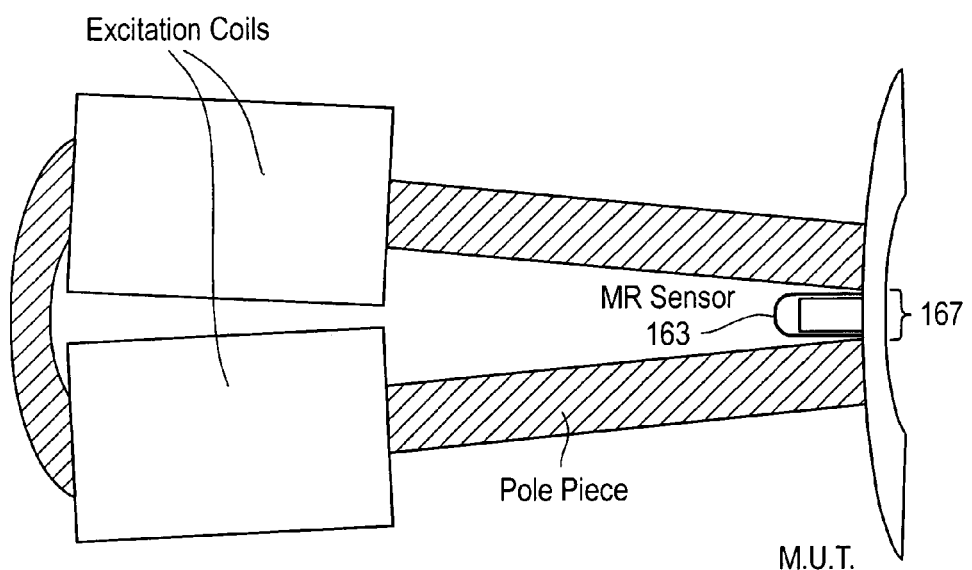

FIG. 4A is a simplified side view of one embodiment of a magnetic field generator 105a according to one embodiment of the present invention. Magnetic field generator 105a includes first and second pole sections 160a and 160b. Magnetic field generator may be manufactured from a variety of material and a variety of sizes. According to one embodiment, the pole section of the magnetic field generator may be a ribbon shaped core approximately 1 cm long by approximately 0.5 cm wide by approximately 0.025 cm thick. The pole pieces may be formed from high magnetic permeability materials, such as silicon steel, ferrite or other suitable ferromagnetic material. The magnetic field generator 105a might further include a pair of excitation coils 162 wrapped respectively around the pole pieces. The excitation coils may be driven by direct current or alternating current to enhance the magnetic field directed by the pole pieces into the circuit. Between the pole pieces, one or more magnetic field sensors 110 may be advantageously positioned to detect applied magnetic field 120 generated by the magnetic field generator and induced magnetic fields 132 (see FIG. 1). Magnetic field generator 105a may include one or more magnetic shields 163 (see FIG. 4B) disposed between the pole pieces and the magnetic fields sensors.

The contour of pole pieces 160a and 160b may be advantageously set to focus the applied magnetic field in circuit 125. The magnetic susceptibility of typical conductors used for circuits is substantially different from the magnetic susceptibility of the gap 167 between the pole pieces. Therefore, the applied magnetic field will be focused in the low reluctance paths through the circuit. Focusing the applied magnetic field concentrates the eddy currents 132 in the conductive portions of the circuit in close proximity to the gap. Inhomogeneities in the conductors due to thickness variations, cracks, or other defects alter the flow and concentration of the eddy currents and their counter magneto-motive force (described above in detail). This variation in magnetic field strength near the gap produces magnetic field gradients along the length of the gap. The magnetic field sensors are configured to detect these magnetic field variations.

According to a specific embodiment, the pole pieces are soft iron and the coils are driven at frequencies up to about 20 kHz. The pole pieces tend to saturate at about 25 amp turns, therefore each coil has approximately 243 windings of approximately #34 magnet wire and current through the series connected coils is driven to approximately 100 milliamps or less (i.e. about 400 circular mils per amp). Magnetic field generators 105a may be fabricated by one or more semiconductor fabrication processes (e.g., photolithography processes, plasma deposition processes, etc.), ion-beam etching processes, micro-machining processes, nano-machining processes or the like.

Figure 5:
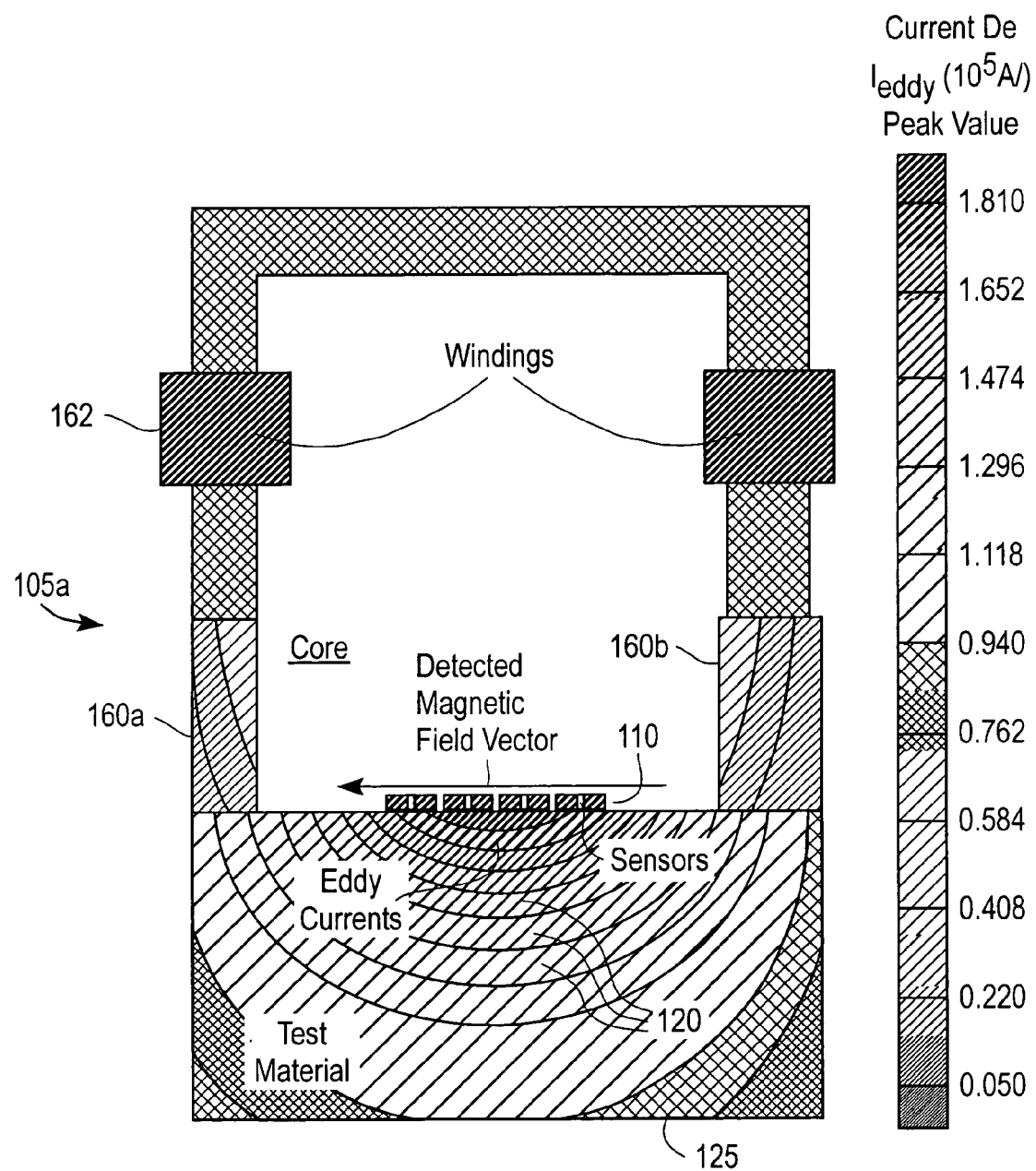
FIG. 5 is a simplified side view of magnetic field generator adjacent to a circuit according to another embodiment of the present invention.
Figure 6A:
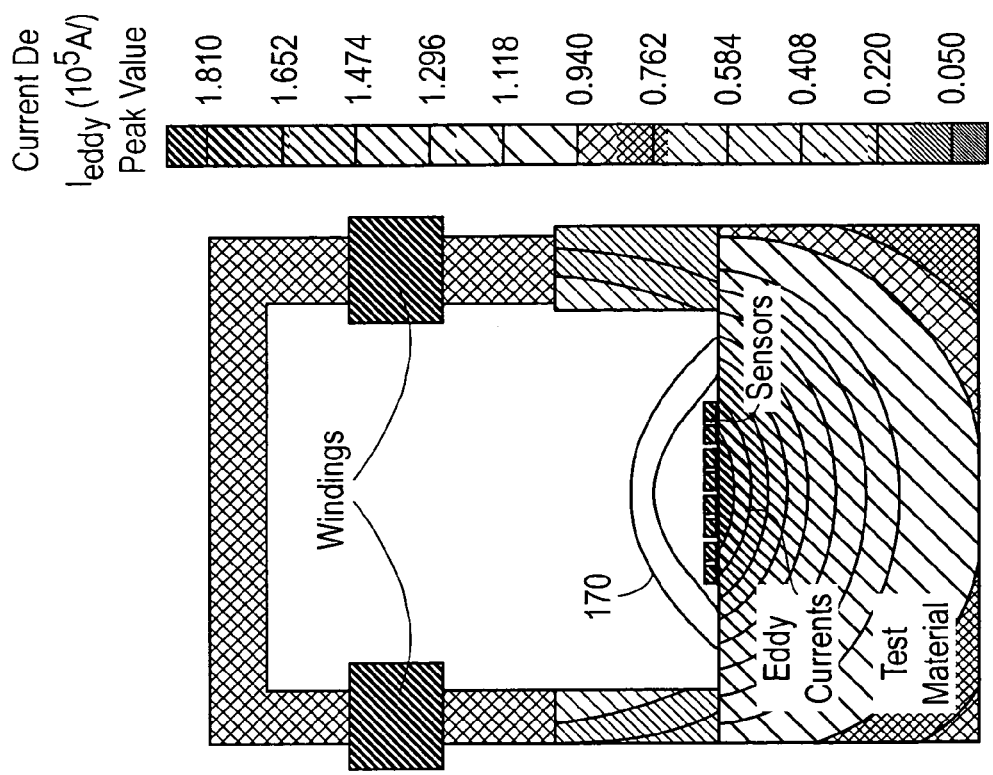
FIGS. 6A and 6A are simplified side views of the magnetic field generator with magnetic shielding.
Figure 6B:
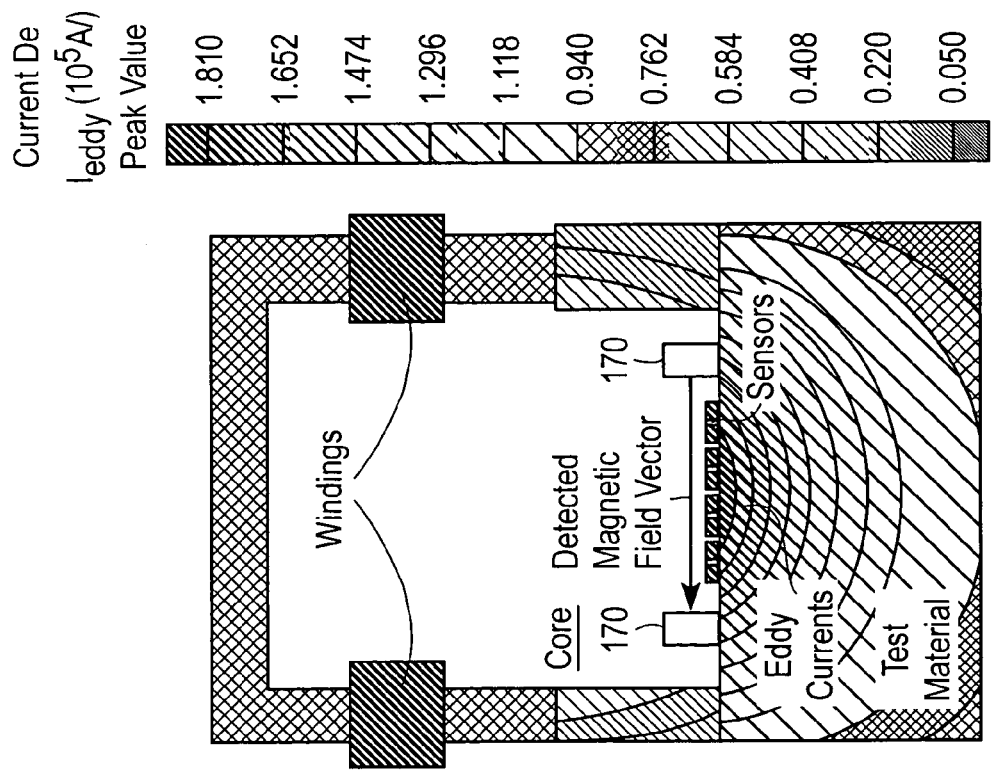

FIG. 5 is a simplified side view of magnetic field generator 105a adjacent to circuit 125. FIG. 5 shows the substantial uniformity of magnetic field 120 at various vertical positions in the circuit. According to the embodiment of FIG. 5, a plurality of magnetic fields sensors 110 are disposed between pole pieces 160 to detect the induced magnetic fields. One or more magnetic shields 170 (see FIG. 6A) may be disposed between the pole pieces and the magnetic field sensors to substantially block magnetic field line 120 that are parallel to the plane of the sensor's magnetic sensitive axis from reaching the sensors. The magnetic shield may be composed of individual shield elements or might be a single shield element that forms a ring that surrounds the sides of the sensors. While magnetic shields 170 are shown in FIG. 6A as being disposed on either side of the sensors, magnetic shield 170 might be configured to also shield the tops of the sensors as shown in FIG. 6B. The magnetic shields may be soft ferromagnetic material or the like that is configured to block magnetic fields. Shielding the sensor advantageously reduces magnetic noise detected by the sensors.

FIG. 7A is a simplified top view of one embodiment of a plurality of magnetic field generators 105b according to one embodiment of the present invention. FIG. 7B shows an enlarged view of one of the magnetic field generators 105b. Each magnetic field generator 105b is a coil disposed substantially around one or more magnetic field sensors 110. Each magnetic field sensor 110 might be partially surrounded (e.g., in the plane of the coils) by a magnetic shield 175 that is configured to shield the sensor from the magnetic fields generated by the coils. Additionally, each end of each magnetic field sensor may be coupled to a pole/flux gate 177.

Each coil may be disposed substantially parallel to surface 140 (see FIG. 1) or might be advantageously disposed at another angle to substantially optimize the induction of eddy currents 130 in circuit 125. The coils might be superconducting coils, metal coils or the like. For example, the coils might be formed of gold, aluminum, nickel, copper, platinum, a combination thereof or other metals. The coils might be formed in a semiconductor manufacturing process at substantially the same time that the magnetic field sensors are formed (e.g., as circuit 150 is formed). Alternatively, the coils, the magnetic field sensors, the shields, and/or the pole/flux gates might be formed in a machining process (e.g., a micromachining process, a nanomachining process or the like).

The foregoing described magnetic field sensors and/or their associated magnetic field generators may be activated according to a select pattern and for select periods of time. The select period of time any given magnetic field sensor and/or magnetic field generator is activated may be independent of the activation times of other sensors and generators. Moreover, the magnetic field sensor and/or magnetic field generators may be activated according to a select pattern to introduce a select pattern of magnetic fields in the circuit. The select pattern might be associated with portions of a circuit that are likely to be defective. Strategically selecting an activation pattern and/or detection pattern provides for the relative rapid collection of magnetic field data from circuit regions that have relatively high likelihoods of being defective, and provides for limiting imaging portions of a circuit known to be relatively free of defects.

Figure 8:
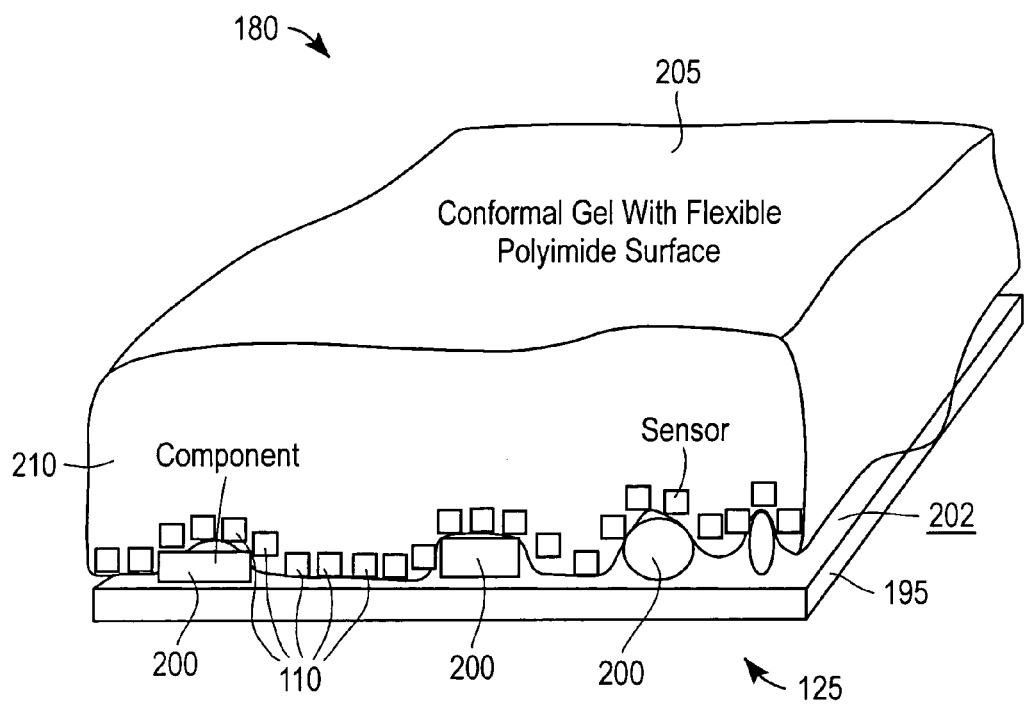
FIG. 8 is a simplified perspective view of a set of magnetic field sensors coupled to a flexible substrate.

FIG. 8 is a simplified perspective view of a set of magnetic field sensors 110 coupled to a flexible substrate 180 according to one embodiment of the present invention. Flexible substrate 180 might be formed of polyimide, polyamide, or the like 205 on a gel polymer 210. The magnetic field sensors might be disposed in the gel polymer. The flexible substrate is configured to adapt the profile of the magnetic field sensors to the shape of the circuit being tested. In the particular embodiment of FIG. 8, circuit 125 includes a PCB 195 having a number of circuit elements 200 or the like attached thereto and that rise above the surface 202 of the PCB. The flexible substrate permits the sensors to move relatively close to the PCB and the circuit elements to advantageously defect a relatively large amount of the magnetic field lines induced in the circuit.

Figure 9:
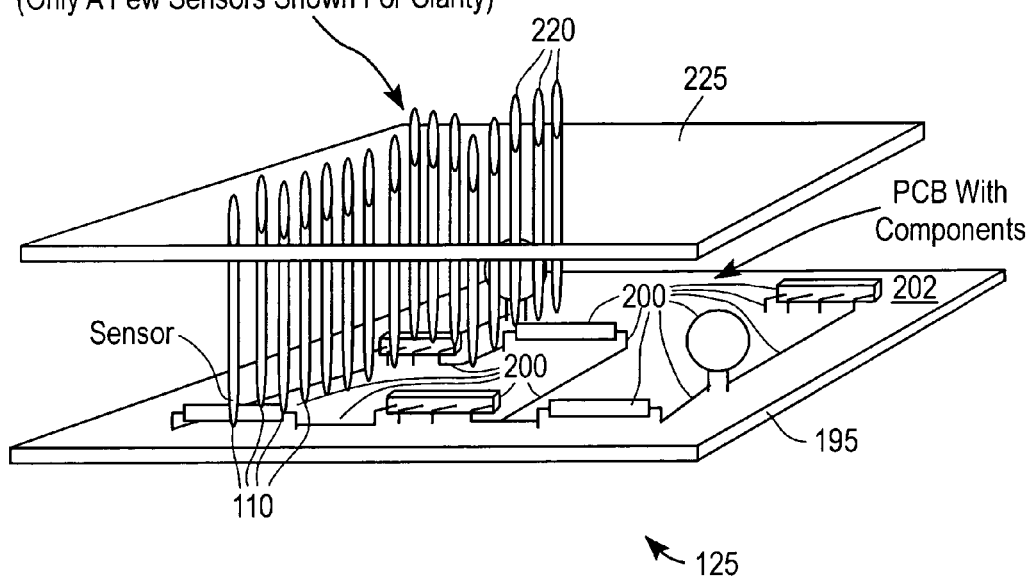
FIG. 9 is a perspective view of a set of magnetic field sensors coupled to a set of "nails" forming a portion of a "bed of nails" device.

FIG. 9 is a perspective view of a set of magnetic field sensors 110 coupled to a set of "nails" 220 forming a portion of a "bed of nails" device. The nails are configured to move up and down, for example, in a guide 225 that includes a number of holes (not shown) that permit the nails and the magnetic field sensors to substantially adapt to the shape of PCB 195 and circuit elements 200.

Figure 10A:
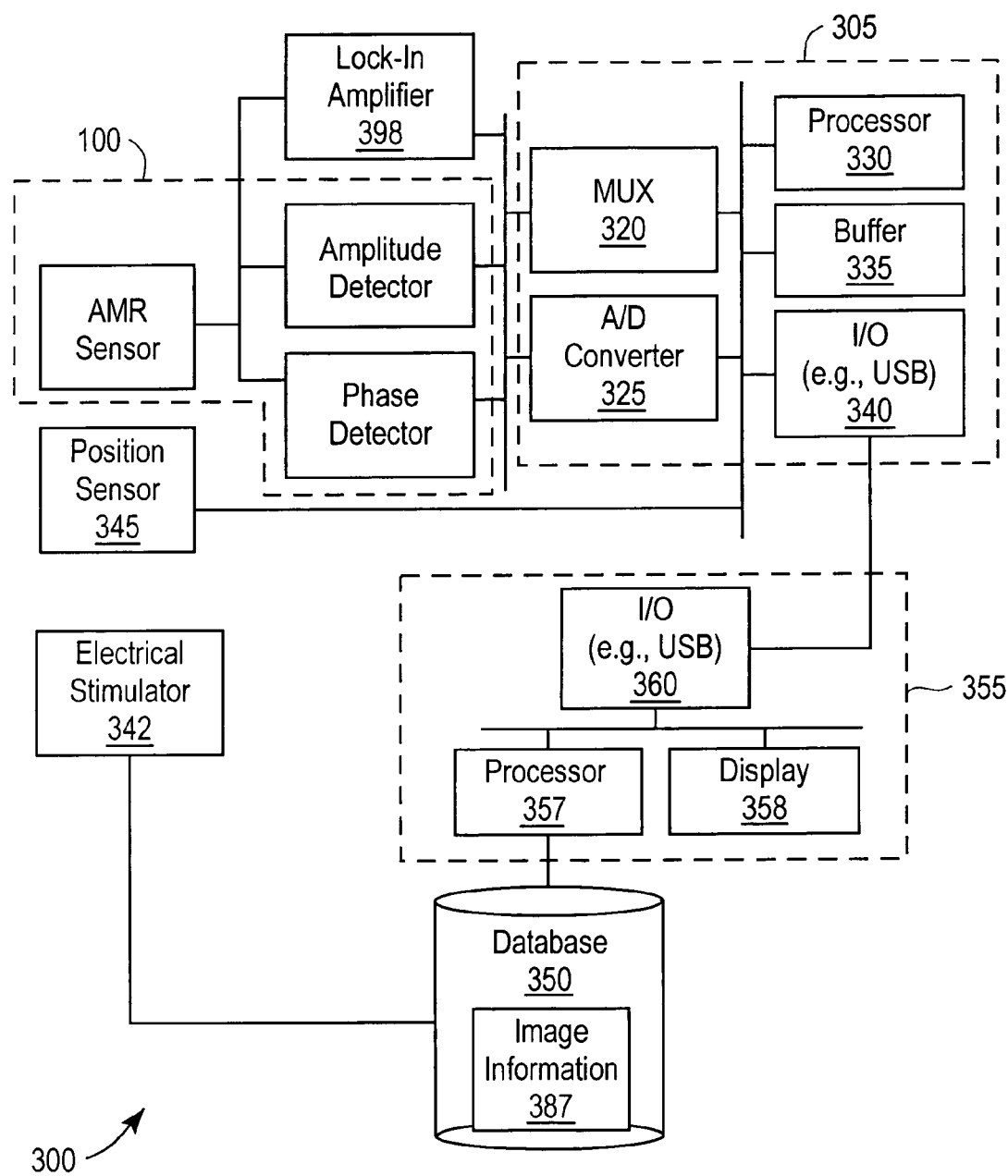
FIG. 10A is a simplified block diagram of a material analysis system configured to generate image data and images of a material having at least one conductive portion.
Figure 10B:
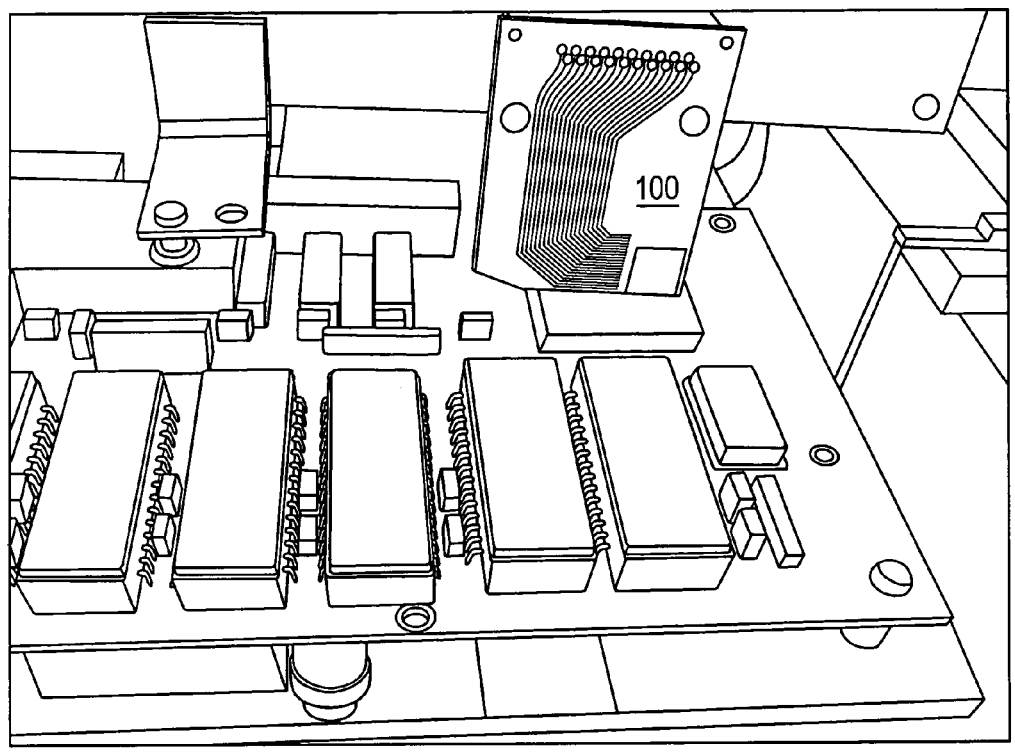
FIG. 10B is an image of a specific embodiment of the dual mode magnetic imager 100 disposed adjacent to a circuit on a PCB.

FIG. 10A is a simplified block diagram of a material analysis system 300 configured to generate image data and images of circuit 125 and specifically of conductors 135 according to one embodiment of the present invention. The material analysis system 300 includes a DMMI 100 and at least one computer 305. Computer 305 may be a PDA, a laptop computer, a desktop computer, circuitry that is disposed in part or in whole on circuit 150 (see FIG. 3) or the like. Computer 305 includes one or more of a multiplexer 320, an analog to digital (A/D) converter 325, a processor 330 (e.g., a microprocessor or microcontroller), a memory 335, and an interface device 340 (e.g., a USB port, a modem, an RF node [e.g., a WiFi node, a Bluetooth node, Home RF, a cell phone link, a dedicated web enabled link, etc.], an IR node, etc.). According to some embodiments, the phase detector 115 and/or the amplitude detector 117 might be configured to form a portion of the computer. It will be appreciated by those of skill in the art that the various modules described herein may be variously combined without deviating from the scope and purview of the invention. FIG. 10B is an image of a specific embodiment of DMMI 100 disposed adjacent to a circuit 337 (e.g., IC) that is disposed on a PCB 338.

The material analysis system 300 may include an electrical stimulation unit 342 that may be configured to apply one or more voltages and or currents to circuit 125. The electrical stimulation unit may be configured to supply power (e.g., VCC) to the circuit, and input signals to the I/O contacts of the circuit. The electrical stimulation unit may include a variety of devices configured to operate the circuit, such as another circuit (e.g., IC, PCB, etc.), a test fixture or the like.

Material analysis system 300 may further include a position sensor 345 configured to detect the distance of the sensors from the surface of circuit 125. The position sensor may be a contact device (e.g., a solenoid, micrometer, etc) configured to contact circuit 125, or a non-contact device (e.g., a sonic reflection device, an ultrasonic reflection device, a magnetic field sensing device, an optical interferometer (e.g., a laser interferometer), or other optical or acoustic metrology device). The position sensor may be configured to position the magnetic field sensors a substantially fixed distance from the circuit. According to a specific embodiment, the position sensor is configured to control the position and/or orientation of translation device 145 (see FIG. 2), and thereby control the position and the orientation of the magnetic field sensors above circuit 125.

According to a further embodiment, position sensor 345 may also be configured to collect information for the position of the magnetic field sensors with respect to the circuit. For example, the position sensor may be configured to collect information for the distance between the sensors and the circuit, and/or collect information of the orientation (e.g., parallel, deviations from parallel, etc.) of the sensors relative to the circuit. The position sensor may be configured to transfer the distance information and/or the orientation information to the computer (e.g., memory 335) and/or a database 350 for subsequent retrieval by the computer. The computer may be configured to use the distance information and/or the orientation information to normalize the collected image data to a set distance. The set distance might be an average distance or other select distance between the magnetic field sensors and the circuit.

According to one embodiment, material analysis system 300 includes a second computer 355 that might be a relatively more "powerful" computer than computer 305, which may be configured to transfer raw data or partially processed data to computer 355 via the interface device for image generation and analysis. Computer 355 may include a processor 357, a display 358, and an interface device 360 (e.g., a USB port, a modem, an RF node [e.g., a WiFi node, a Bluetooth node, Home RF, a cell phone link, a dedicated web enabled link, etc.], an IR node, etc.) that is configured to communicate with interface device 340 of computer 305. Computer 355 may be remotely disposed with respect to computer 305, and the interface devices of these computers may be configured to communicate via a network (e.g., the Internet, an intranet, a virtual intranet, etc.) that provides a communication link between these computers. One or both of computers 305 and 350 may be coupled to database 350 that includes circuit information relevant to one or more circuits under test. The foregoing described elements of material analysis system 300 are described in further detail below as these elements become relevant in the following description of image formation. It is briefly noted, however, that the foregoing described elements of imaging system 300 may be hardware devices, software, firmware devices or a combination of the foregoing. Subsequent to the review of the description herein taken in combination with the appended drawings and the claims, those of skill in the art will be readily able to use one or a combination of hardware devices, software, firmware devices or the like to make and use material analysis system 300.

As described briefly above, material analysis system 300 is configured to generate an image of circuit 125 via image information collected via the induced magnetic fields 132 (see FIG. 1). As described briefly above, in the presence of applied magnetic field 120, eddy current 130 are generated in conductors 135 of circuit 125. In the central portions of the conductors, the eddy currents tend to be substantially uniform, and at the edges of the conductors the eddy currents tend to compress. The compressed eddy currents along the edges of the conductors generate induced magnetic fields that are generally larger than the eddy currents that form in the central portions of the conductors. As the induced magnetic fields generated at the edges of the conductor are relatively high compared to the inducted magnetic field generated at the central portions of the conductors, the magnetic field sensors 110 can detect this induced magnetic field variation. Further, as the material surrounding a conductor may be non-conductive (i.e., dielectric), the applied magnetic field will not induce eddy current formation and therefore not generate induced magnetic fields. The magnetic field sensors are configured to detect these decreases in magnetic field in the central portions of the conductors and in the material surrounding the conductors. For example, one magnetic field sensor that is substantially over the edge of a conductor will exhibit a relatively large change in resistant in response to sensing a relatively large induced magnetic field along the edge, and an adjacent magnetic field sensor that is over a non-conducting portion of the circuit that is adjacent to the conductor, or that is over a central portion of a conductor, will exhibit no resistance change or exhibit a relatively smaller resistance change. This disparate magnetic field information collected by the sensors may be used by computer 305 and/or computer 355 to generate an image of circuit 125, or more specifically of conductors 135.

The disparate magnetic field intensity information collected by the magnetic field sensors is advantageously used by the material analysis system to generate images of the conductors in the circuit such that the images of the conductors include images of the conductor defects. To elaborate, conductor defects that are detectable and imaged by the material analysis system include voids in a conductor (both along the edges of a conductor and in the central portions of the conductor), cuts, tears, opens and other defects. Further, portions of the conductors that are relatively thinner or relatively thicker than other portions of a conductor are also detectable and imageable. Specifically, induced eddy currents tend to condense along the edges of defects similar to the way eddy currents condense along other edges of the conductors. Further, the induced eddy currents also tend to condense in the thinner portions of the conductors as compared to relatively thicker portions of the conductors. As the eddy currents tend to condense at defect edges, and in relatively thin conductor portions, the magnetic field sensors can detect the relatively high magnetic fields generated by these condensed eddy currents. Therefore, images generated by the material analysis system of these conductors will include image information for the conductor's defects. Image generation methods are described in detail below.

Figure 11:
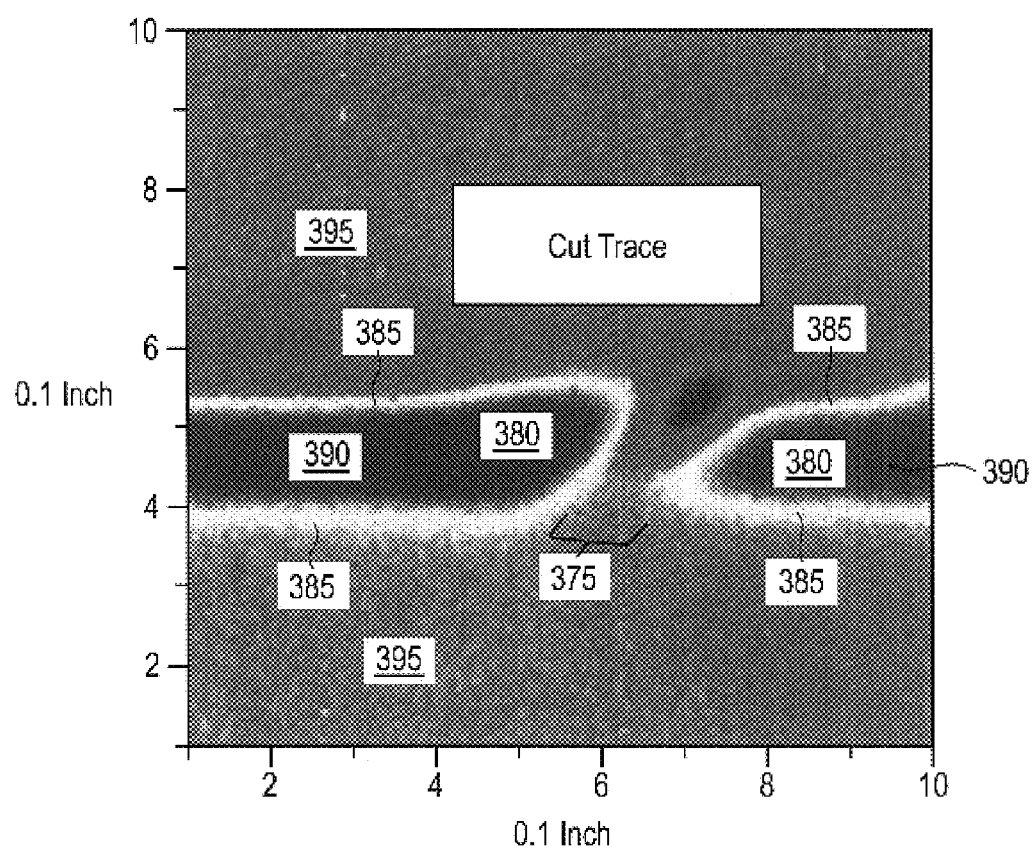
FIG. 11 is a simplified image of a conductor (e.g., a circuit trace) that has a cut.

Images of circuit 125 may be presented to the user on a display (not shown) of computer 305, on display 358 of computer 355 or the like. FIG. 11, for example, is a simplified image of a conductor 370 (e.g., a circuit trace) that has a cut 375. The charge accumulation at the cut edges 380 and edges 385 generates relatively large magnetic fields compared with the central portions 390 of the conductor and the surrounding dielectric 395. This difference in magnetic field strength may be detected by the set of magnetic field sensors and imaged by the material analysis system.

According to some embodiments, the magnetic field sensors are configured to detect defects of approximately one micron or less (e.g., a half or quarter of a micron). According to one relatively high resolution embodiment (e.g., micron and sub-micron analysis and/or image generation), data resolution may be relatively enhanced via the operation of one or a relatively few disparately positioned magnetic field sensors. For example, one magnetic field sensor and its associated magnetic field generator (e.g., generators 105*a* or 105*b*) may be operated so that the magnetic field sensor does not substantially detect, e.g., as background noise, the applied magnetic fields of other magnetic field generators. Processor 330 might be configured to control multiplexer 320 that in turn may be configured to selectively activate one or more magnetic field generators and/or selectively activate (e.g., apply a bias voltage) one or more magnetic field sensors based on instructions received from the processor.

According to one embodiment, amplitude detector 117 is configured to detect the strength of the magnetic fields detected by the magnetic field sensors. Specifically, the amplitude detector might be a voltage meter or a current meter that is configured to detect the resistance change of the magneto-resistive sensors that are in the presence of an applied magnetic field (e.g., magnetic field 120 and/or 132). The analog amplitude information output from the magnetic field sensors might be processed by one or more processing devices (not shown), such as a low pass filter, a band pass filter, etc., and thereafter amplified by a amplifier circuit (not shown). According to one embodiment, the processed amplitude information output from the processing device is a continuous analog voltage that is proportional to the magnetic fields detected by the set of magnetic field sensors. The amplitude information is subsequently digitized by A/D converter 325, and the digital amplitude information output from the A/D converter is transferred to memory 335, database 350 or the like for subsequent transfer to computer 305 and/or to computer 355 or for processing. Alternatively, the digital amplitude information may be transferred to one or both of the computers in substantially real time for processing. The memory might also be configured to store program code that might be transferred to one or both of computers 305 and 355 for image generation of the circuit and/or for analysis (e.g., fault detection) of the digital amplitude information. The digital amplitude information for the magnetic fields may be analyzed (e.g., in substantially real time) by the computer to determine one or more of the magnetic field amplitude, the magnetic field sensor sensitivity, the sensor noise, the sensor settling time, and one or more filtering parameters. Based on the foregoing described determinations, computer 305 and/or 350 may adjust the amount of time magnetic field information is collected by the system. For example, if the material analysis system is configured to collect magnetic field information from the magnetic field sensors for a period of time, but the signal to noise ratio falls, this period of time may be extended to collect additional information, or the collection of the magnetic field information may be repeated. If the magnetic field sensors are programmed to be sweep across the surface of the circuit, the magnetic field sensors may be held in place for a relatively longer time period ("dwell time") to collect additional magnetic field information each time the sensors are stopped to collect amplitude information of the magnetic fields.

According to one embodiment, phase detector 115 is configured to determine the phase difference between the applied magnetic field 120 and induce the magnetic field 132. The phase detector may also be configured to discriminate between the magnetic fields having different phases. The phase angle between the applied magnetic field 120 and the induced magnetic field 132 indicates the depth from inside the circuit (z-axis height) at which the induced magnetic field is generated. Specifically, the change in phase of the induced magnetic field is a function of the amount of material the applied magnetic field and the included magnetic field traverse. Therefore, by computer analysis of the phase difference between the induced magnetic field having a specific phase relationship with the applied magnetic field, a specific layer of conductors within a circuit may be analyzed for defects and images generated for this specific layers of conductors. Therefore, by computer analysis of a plurality of induced magnetic fields having a plurality of phase relationships with the applied magnetic field, a plurality of conductor layers may be analyzed for defects and images generated for these conductor layers. Thereby, a three-dimensional analysis may be performed for each of the conductor layers in a circuit and a two-dimensional image and/or a three-dimensional image may be created for the conductor layers. As three-dimensional analysis may be performed, conductors that are laterally disposed as well as conductors that are vertically disposed (e.g., vias) may be analyzed for defects.

To further enhance image generation and analysis of a specific conductor layer, the frequency of the applied magnetic field may be chosen such that the magnetic field has "optimal" penetration for the specific conductor layer to induce charge movement in the specific conductor layer. For example, a relatively low frequency (e.g., approximately 1 kHz) applied magnetic fields may be applied to the circuit to analyze conductor layers (e.g., a first metal layer or the like) that are relatively deep in a circuit, and relatively higher frequency (e.g., approximately 50 kHz to approximately 100 kHz, inclusive) magnetic fields may be applied to a circuit to analyze conductor layers (e.g., bonding pads, wire bonds, etc.) that are close to the top of the circuit. By progressively stepping the applied magnetic field through a range of frequencies, each of the conductor layers between the top conductor layer and the bottom conductor layer may be imaged and analyzed for defects (described below in further detail). Such analysis provides relatively precise x, y, z positions of defects within a circuit.

Circuit Operation Imaging

According to one embodiment of the present invention, induced magnetic fields 132 are induced in the circuit by operating the circuit. As is well understood by those of skill in the art, a circuit is generally operated by placing select voltages and/or currents on the circuit's electrical contacts. The electrical contacts may include I/O contacts, VCC contacts, ground contacts and the like. Depending on the circuit's particular package, the I/O contacts, the VCC contacts, and the ground contacts may include solder bumps, solder balls, package leads, solder pads, bond pads, wire bonds, lead frames, etc. In the particular case of a PCB, the I/O contacts, the VCC contacts, and the ground contacts may include sockets (e.g., edge connectors, SCSI connectors, etc), contact pads, edge connectors, etc. For example, a circuit might be powered on and powered down a number of times to image and analyze powering on the circuit and/or powering down the circuit.

Via operation of the circuit, the circuit elements of the circuit shape the flow of current through the circuit. The circuit elements may include nearly any conducting element through which current may flow in the circuit. For example, circuit elements may include conductive traces (e.g., metal lines), transistors, vias, wire bonds, bond pads, analog circuit elements (e.g., inductors, capacitors, resistors, etc) and the like.

Current passing through circuit elements generates magnetic fields 132 that can be detected by the magnetic field sensors 110. The magnetic field information collected by the magnetic field sensors may be transferred to computer 305 and/or computer 355, which in turn are configured to analyze the collected magnetic field information to generate images of the circuit and therefrom analyze the circuit for defects. From the collected magnetic field information, the material analysis system may generate one or more images of the operating circuit elements. A generated image may include a "snap shot" of the circuit (or portion thereof) for a particular instant of circuit operation, or may include a series of snap shots that may be a "movie" of circuit operation over a period of circuit operation.

The material analysis system may sequentially display the generated images on the display of computer 305 or computer 355. The generated images may be displayed for a select period of time and at a select time interval. The time interval between image display might be associated with the cyclic operation of the circuit (e.g., a power cycle) of other select time interval (e.g., approximately 10 nanoseconds to approximately 30 milliseconds or longer). Displaying images of the circuit over a select time interval and for select periods of time, provides that a user may "view" the circuit in operation and view any defective operation thereof. Accordingly, the user may detect defects that otherwise might be difficult to detect or undetectable by standard electrical contact testing of the circuit.

As described briefly above, the circuit may be repeatedly operated, for example, by repeatedly applying substantially the same stimulus to the circuit in a repeating manner. For example, the circuit may be powered up and powered down a number of times at a select frequency (e.g., substantially sinusoidally at about 25 Hz and at about a 50% duty cycle). Or the I/O contacts of the circuit may be driven with substantially the same set of vectors (i.e., drive states and/or compare states of the I/O contacts) a number of times.

Figure 12:
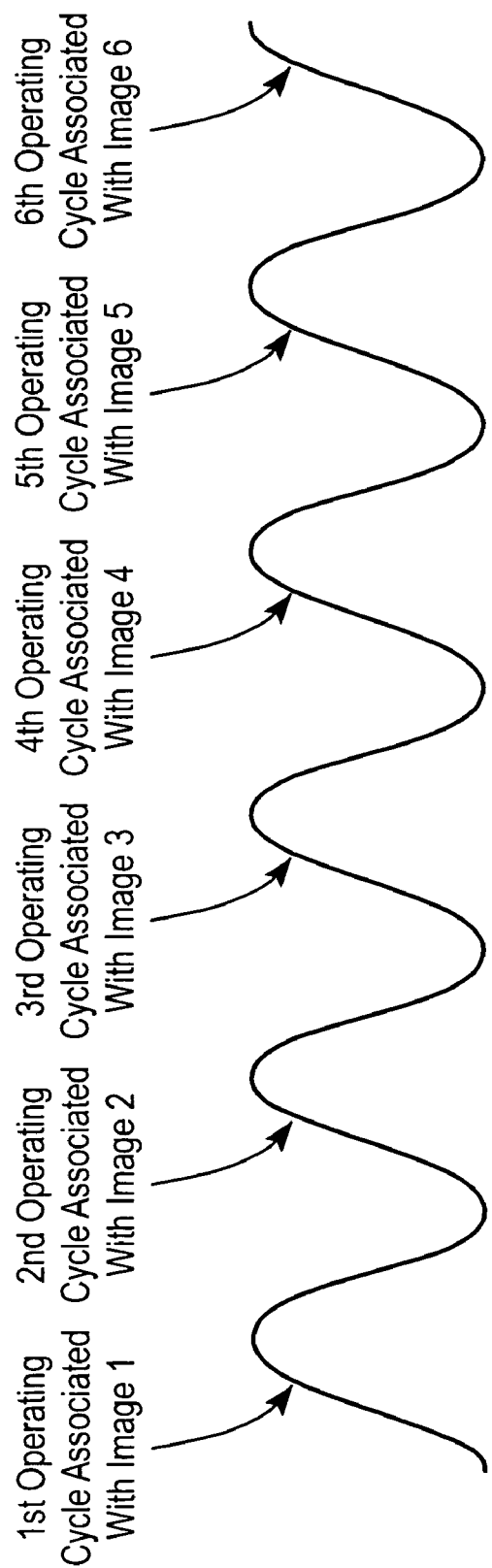
FIG. 12 is a simplified diagram of a sinusoidal operating signal and shows a number of positions on the signal associated with a number of generated images.

According to one embodiment, the material analysis system is configured to temporally correlate a number of generated images to the cyclic operation of the circuit. The material analysis system thereafter is configured to aggregate the correlated images to generate an aggregated image. To elaborate, generated images and or image data may be correlated to the stimulus cycle of the circuit, such as a power up and power down cycle, the cycling of one or more I/O contacts, or a clock signal, which may or may not be applied to the circuit. Each stored image frame may be associated with a stored cycle indicia (e.g., stored in database 350 and/or memory 335) that indicates the temporal position and/or phase position at which the image frame was generated with respect to the periodic reference signal. The cycle indicia may indicate that the images were generated, for example, at the peak of a duty cycle, 25 degrees before the peak, 37 degrees after the peak, every 25 millisecond, every 10 nanoseconds or the like. FIG. 12 is a simplified diagram of a sinusoidal signal (e.g., a clock signal, a signal having the same frequency as a power up and power down, a vector operation cycle, etc.) and shows a number of positions on the signal associated with a number of generated images. These images may be aggregated by the material analysis system as the images are associated with the same phase in the operation cycle. According to'one embodiment, the cycle indicia may also include information for the length of time (e.g., from 1 nanosecond up to 1 millisecond or greater) over which image data for each image frame is collected by the material analysis system.

According to one embodiment, the material analysis system includes a lock-in amplified 398 that is used by the system to enhance correlation between i) the circuit stimulus, ii) the analog amplitude information collected by the set of magnetic field sensors or the digitized amplitude information if the lock-in amplifier is a digital device, and iii) the generated images of the circuit. The lock-in amplifier provides that amplitude information and/or the images generated for a number of operation cycles may be advantageously averaged to improve the signal to noise ratio. Specifically, the raw analog amplitude information collected via the magneto-resistive sensors may be in the nanovolt range, and may be buried in tens of nanovolts of noise to over 100 millivolts of noise. The noise signal is attributable to any number of magnetic noise sources, such as light, motors (e.g., stepper motors), electrical lines and the like. The lock-in amplifier output, according to one embodiment, is a time varying DC signal that represents the output of the magnetic field sensor at the circuit operation frequency with substantially all other frequencies squelched.

Lock-in amplifier 398 may be used for both magnetic field amplitude (e.g., via voltage and/or current changes of sensors 110) measurements and magnetic phase measurements buried in noise. The lock-in amplifier is used as a narrow bandpass filter that serves to remove unwanted noise while permitting the desired magnetic field information to be measured. A signal having a reference frequency (i.e., the bandpass region of the lock-in amplifier) that substantially matches the frequency of the signal to be measured is supplied to the lock-in amplifier along with the signal collected by the magnetic field sensors. A demodulator circuit of the lock-in amplifier multiplies the signal for the reference frequency and the signal collected by the magnetic field sensors. These two waveforms multiplied together represent the two waveform's sum and difference frequencies. As the signal collected by the magnetic field sensors and the signal for the reference frequency are substantially the same frequency, the difference frequency of these two waveforms is substantially zero. The DC output of the lock-in amplifier is proportional to the amplitude of the signal collected by the magnetic field sensors and the cosine of the phase difference between these two waveforms. By adjusting the phase of the signal for the reference frequency using the reference circuit (e.g., free running clock, power up cycle, electrical stimulator), the phase difference between these two waveforms can be forced substantially to zero, and therefore the DC output level from the multiplier is proportional to the signal collected by the magnetic field sensors. As the various noise components on the signal collected by the sensors are at different frequencies than the signal for the reference frequency, the sum and difference frequencies will be nonzero and will not contribute to the DC level of the output signal. This DC level (which is proportional to the signal detected by the magnetic filed sensors) can thereafter be recovered by passing the output from a demodulator through a low pass filter. This process provides that various processing procedures, such as processing algorithms, may be used to select sections of the stimulus cycle that contain select information regarding circuit operation, such as the switching of select transistors, the pattern of current flow at power up, power down, etc.

It should be understood that the foregoing described process may be performed for a number of temporal or phase positions in a number of operation cycles such that a number of images at various temporal positions or phase positions may be corrected to generate a "movie" of circuit operation, wherein each "frame" includes aggregated images for each particular cycle position of interest.

While the foregoing describes the aggregation (i.e., summation) of images over a number of temporally correlated positions in a number of operating cycles, correlated images might also be subtracted. A circuit image generated by the subtraction of one or more temporally correlated images provides information for the differences in circuit operation across a number of operating cycles (e.g., power cycles, clock cycles, etc.). For example, intermittently occurring circuit defects may be detected via image subtraction. For example, if one image that is associated with an intermittently occurring defect is subtracted from another image that is not associated with the intermittently occurring defect, the defect information in the subtracted images may be one of the few remaining pieces of image information in the subtracted image rendering the defect information relatively easily identifiable.

According to one embodiment of the present invention, the material analysis system is configured to transform image information associated with one or more images into the frequency domain or other domains. For example, image information (e.g., the analog or digital amplitude information for magnetic field 132) may be Fourier transformed via a discrete Fourier transform, a chirp transform or other known transform functions. Spectral information from one or more transformed images may be compared to other transformed images (e.g., for golden units or defective circuits), and/or image information (e.g., stored in the database) for circuit evaluation for defect circuit operation. Images generated by magnetic field induction methods and/or circuit operation methods may be transformed and compared with image information stored in the database and/or with each other.

Image Formation

The digital amplitude information for the detected magnetic fields induced in the circuit are used by the material analysis system to generate images of the circuit, and more specifically of the conductive elements of the circuit. According to one image formation embodiment, location information for each magnetic field sensor in an array of magnetic field sensors is stored in a lookup table in the database. The location information may include information of the relative distances between adjacent magnetic field sensors, x-y positions (e.g., center of the sensors, corner of sensors, etc), and z positions if the sensors are arranged three-dimensionally. The digital amplitude information for detected magnetic fields (e.g., stored as one image frame per page in the database) may be correlated with the location information of the magnetic field sensors for image generation of the circuit. The digital amplitude information correlated with the location information for the sensors is referred to at mapped data. Each image frame may be associated with digital amplitude information this collected substantially continuously (e.g., 1 nanosecond to 1 millisecond or more per frame), or may be a correlated image that includes image information from a number of images correlated at the same phase positions of a number of operating cycles (described above in detail). For example, the location information of the magnetic field sensors correlated with the digital amplitude information may be mapped data that is used by the material analysis system to generate a two-dimensional and/or a three-dimensional image of the circuit. According to one embodiment, the location information for the magnetic field sensors is correlated with one or more of i) the induced magnetic field magnitudes; ii) the induced magnetic field phase variation between the inducing magnetic field and the detected magnetic field; iii) the magnetic field amplitudes generated via circuit operation (e.g., driving current and/or voltage through the circuit); and/or vi) the magnetic phase of magnetic fields associated with current and/or voltage related magnetic field induction.

As the magnetic fields generated in the circuit are sensitive to the edges of the conductor (including defects, such as voids), and as the phase variation provides information for the depth of the conductor, the currently described circuit analysis methods provide that a user or the material analysis system analyzing these data (e.g., images) can determine the geometry of the conductor including its defects, the location of the defects in the circuit in one, two, or three dimensions, and the severity of the defect. The material analysis system or the user of the system may compare the identified defect location with a circuit layout or the like to identify the particular circuit element that is defective in the circuit.

Figure 13:
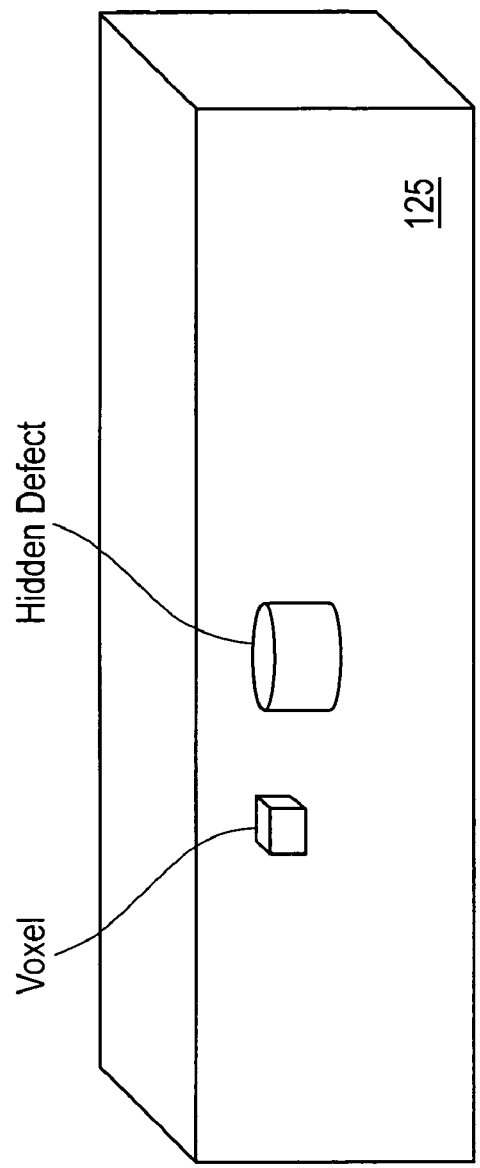
FIG. 13 is a simplified image of a circuit showing a voxel in the circuit that may be associated with generated digital amplitude information for a detected magnetic field.

More specifically, each point in an image frame may be assigned x, y, and z coordinates (or alternatively polar coordinates or circular coordinates if convenient) that are correlated with the magnetic field measurement for that point. More specifically yet, each point in the image frame may also be associated with (or may reference) a voxel of digital amplitude information for detected magnetic fields for the circuit. FIG. 13 is a simplified image of circuit 125 showing a voxel in the circuit that may be associated with generated digital amplitude information. Specifically, a voxel, as referred to herein, is a unit of graphic information (e.g., digital amplitude information) that defines a volume element (hence the term voxel) in three-dimensional space, whereas a pixel (picture element) defines a point in two-dimensional space. The assigned coordinates of a voxel define a location of the voxel in three-dimensional space in the circuit. The sizes of the voxels are defined based on the size of the sensors, measurement geometry, spatial precision of the sensors, and angular precision of the phase measurement. In one example embodiment, each voxel is approximately 100 cubic micrometers.

A set of voxels that are associated with a portion (e.g., a conductor layer) of the circuit, or with substantially the entire volume of the circuit of the part, is stored in the database for use by the material analysis system for image generation. The material analysis system analyses the voxels (e.g., one by one or in parallel) of information to generate two-dimensional or three-dimensional images of the circuit. With the use of three-dimensional rendering software, the material analysis system is configured to generate three dimensional images of the circuit that in essence permits a user to "see" inside the circuit without performing destructive analysis on the circuit. Moreover, as the magnetic field sensors may be made relatively small (e.g., 5×5 micrometers or less), this relatively small size of the magnetic field sensors provide images with "microscopic" (e.g., approximately micrometer resolution) resolution that permits a user and/or the material analysis system to analyze microscopic and nanoscopic defects (e.g., defect signatures).

According to one embodiment, the material analysis system is configured to scale one or more of the generated images and/or digitized amplitude information to adjust for different spatial resolutions that might be associated with the two modes (sometimes referred to herein as dual mode) of magnetic field generation (magnetic induction and circuit operation) and the magnetic field detection associated therewith. As the images may be scaled to the same reference frame, image information for circuit elements is located in the same relative positions in their corresponding images, such that the images may be used in combination for circuit analysis. Generated images and/or digitized amplitude information might also be scaled by the material analysis system to match the size and scale of a PCB layout, an IC layout, a magnified view of one or more masks of a mask set (i.e., IC fabrication mask used in IC fabrication), a design specifications, a conductor map, a CAD image or the like. Image and/or image data scaling can be effected by various software tools that are well known to those of skill in the art. The material analysis system may be configured to display one or more scaled images as superimposed images. For example, a magnetic field induction image may be superimposed over an image generated by circuit operation, such that the circuit element features of the images substantially align. The superposition of images provides that various magnetic signatures may be relatively easily compared by a user or the material analysis system to detect faults in a circuit. The material analysis system may also be configured to display one or more scaled images superimposed over an image of a PCB layout, an IC layout, a magnified image of a mask, a CAD image or the like. Such superposition of images provides that defects can be associated with the circuit elements of a circuit that is imaged by the material analysis system. Associations between superimposed images may be made by a user viewing the superimposed images or by the material analysis system. Identified associations between imaged magnetic fields and an IC layout, for example, provide that imaged magnetic fields can be correlated to the circuit elements that generated the magnetic fields. Specifically, a magnetic signature associated with a circuit defect can be correlated with the particular circuit elements exhibiting the defect behavior. According to one embodiment, the material analysis system running one or more pattern recognition programs (e.g., programs for use with LabWindows) is configured to analyze the scaled and/or superimposed images to automatically identify circuit defects.

The scale (some time referred to as spatial resolution) of generated images and/or the digitized amplitude information can be adjusted by the material analysis system via convolution with a select kernel in the image space, or by multiplication with the select kernel in the spatial frequency domain (i.e., Fourier domain). Scaling can similarly be effected by the material analysis system in the image space by bilinear, cubic or higher order interpolation, or in the Fourier domain.

According to one embodiment, generated images and/or the digitized amplitude information generated may be deconvolved with one or more functions to substantially remove information imposed by the system (e.g., magnetic field sensor shape, position, etc.) onto the images and/or the digitized amplitude information. The images may be deconvolved with the point spread function for the set of magnetic field sensors. Deconvolution may be effected in the spatial domain or the Fourier domain. Deconvolution of the images may provide substantially the same spatial resolution for images associated with both magnetic field induction and circuit operation.

Defect Detection

Computer 305 and/or computer 355 operating alone or in combination may be configured to determine from a set of generated images of circuit 125 (e.g., a circuit) and/or from the digital amplitude information for the circuit whether the circuit is operating properly or is defective. For example, computer 305 may be configured to compare an image of the circuit or compare the digital amplitude information for the circuit with predetermined image information 387 (see FIG. 10) for the circuit. The predetermined image information may be stored in database 350 and retrieved by computer 305 and/or 355 for analysis of the circuit via its associated images and/or digital amplitude information for detected magnetic fields. The predetermined image information may be for a "good" circuit or a defective circuit. A good circuit, as referred to herein, is a circuit that is substantially free of defects and operates substantially as designed, and can be used as a basis for comparison with circuit 125. A defective circuit might be a circuit that has known defects that can be used to identify unknown defects in circuit 125. The predetermined image information in the database may include one or more of images, image data, design specifications, design layouts, a mask set, conductor maps, etc. that may be used for comparison with the circuit images and/or the digital amplitude information to determine whether the circuit has a defect. The nature of the detected defects, images of the defects, locations of the defects and the like may be displayed on the display of computer 305 and/or computer 355.

Various programs (e.g., pattern recognition programs) may be configured to compare the generated images and/or the digital amplitude information with the image information retrieved from the database for defect identification. The images and/or digital amplitude information may be analyzed using programs developed to run with LabWindows™, Matlab™, UNICA™, and/or a dedicated program. The programs may execute various pattern recognition methods to locate circuit defects. Further, images of circuit 125 may also be generated from the digital amplitude information by the computer executing one or more programs configured to run in Matlab™. LabWindows might be used to display generated images on the display. These programs may be run on computer 305, may be run on computer 355 (if, for example, computer 305 has insufficient computing power to run such programs, and/or may be run in combination on computer 305 and computer 355.

According to one embodiment, the material analysis system is configured to determine an amount of deviation from correct operation of the circuit and determine the anticipated time the circuit will operate until failure.

Example Analysis

Figure 14B:
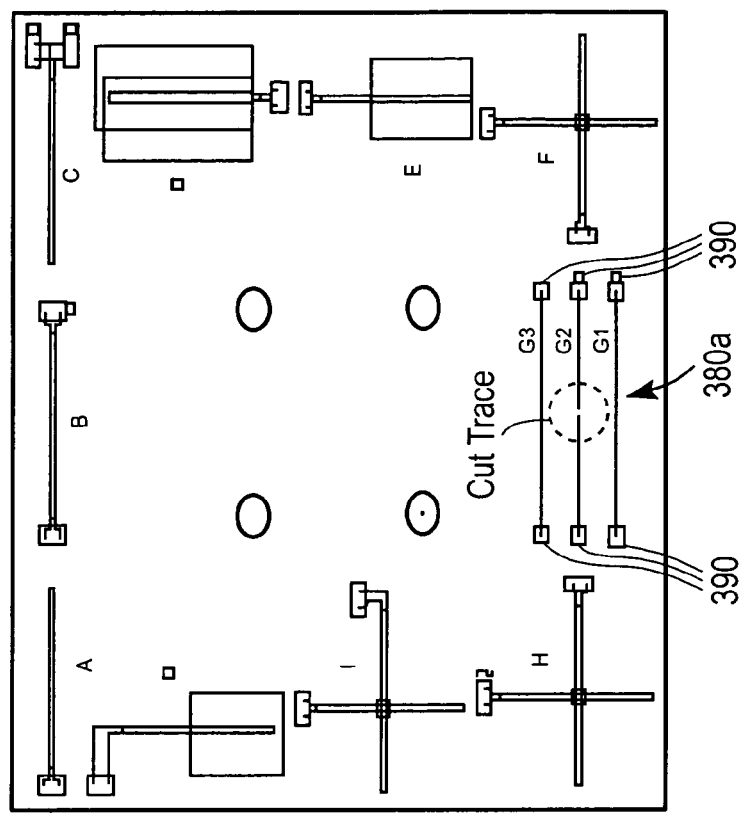
FIGS. 14A and 14B are simplified circuit diagrams of PCBs having an intact trace and a cut trace, respectively.
Figure 14A:
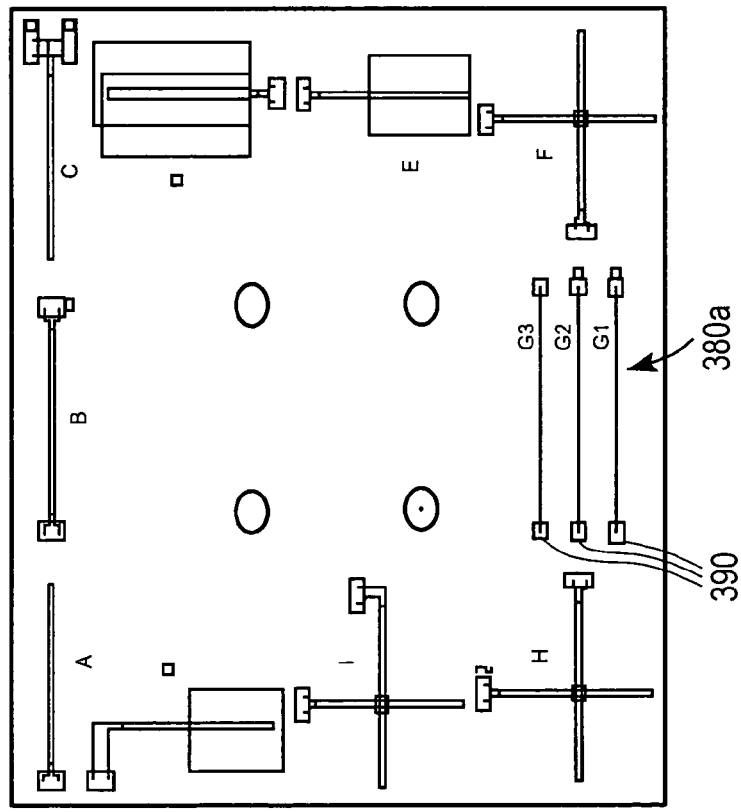
Figure 15A:
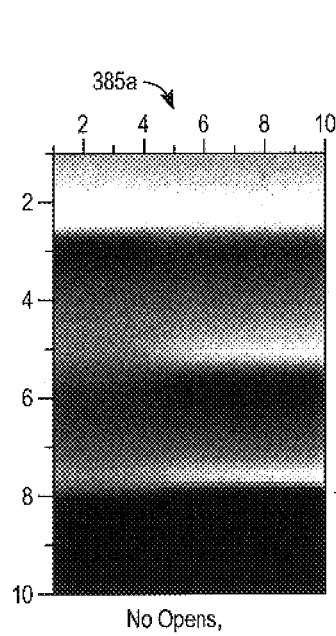
FIGS. 15A and 15B are simplified images of the PCBs shown in FIGS. 14A and 14B.
Figure 15B:
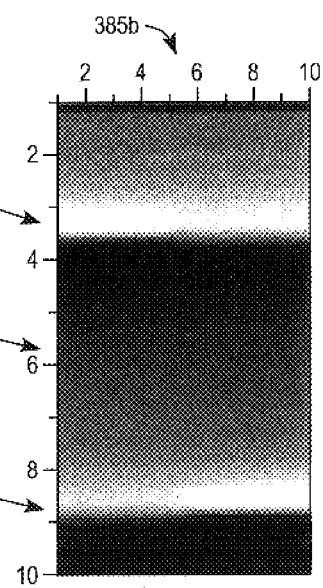

FIGS. 14A and 14B are simplified circuit diagrams of PCBs 380a and 380b, respectively. The PCBs include three traces 01, 02, and 03 in a bottom portion of the PCBs. Trace 02 of circuit boards 380b is cut, whereas trace 02 of PCB 380a is not cut. FIGS. 15A and 15B are simplified images 385a and 385b of circuit boards 380a and 380b, respectively, that might be generated by material analysis system 300. FIG. 11 is a magnified image of the cut in trace 02 of circuit board 380b.

Current may be driven through the traces by a set of contact pads 390 on the circuit boards to include a magnetic field that is detectable by the magnetic field sensors for image generation of the traces. Specifically, in image 385a of FIG. 15A, images traces 01, 02, and 03 of PCB 380b are shown as current may be driven through each trace, and a magnetic field detected from these currents. In image 385b of FIG. 15B, images of the top trace 01 and the bottom trace 03 of PCB 380a are shown as current may be driven through these traces, whereas an image trace 02 is not is not shown because trace 02 is cut and current is not driven across this trace, and therefore, substantially no magnetic field is generated in this trace. The trace may be cut, for example, if the left and right side of the traces are disposed on different layers of the PCB and a via coupling the traces is open, or if the trace is on one layer of the PCB and the trace is cut or the like. While the foregoing description provides an example of a circuit with an open trace that may be detected by the material analysis system, shorts may also be detected by the material analysis system.

Figure 16:
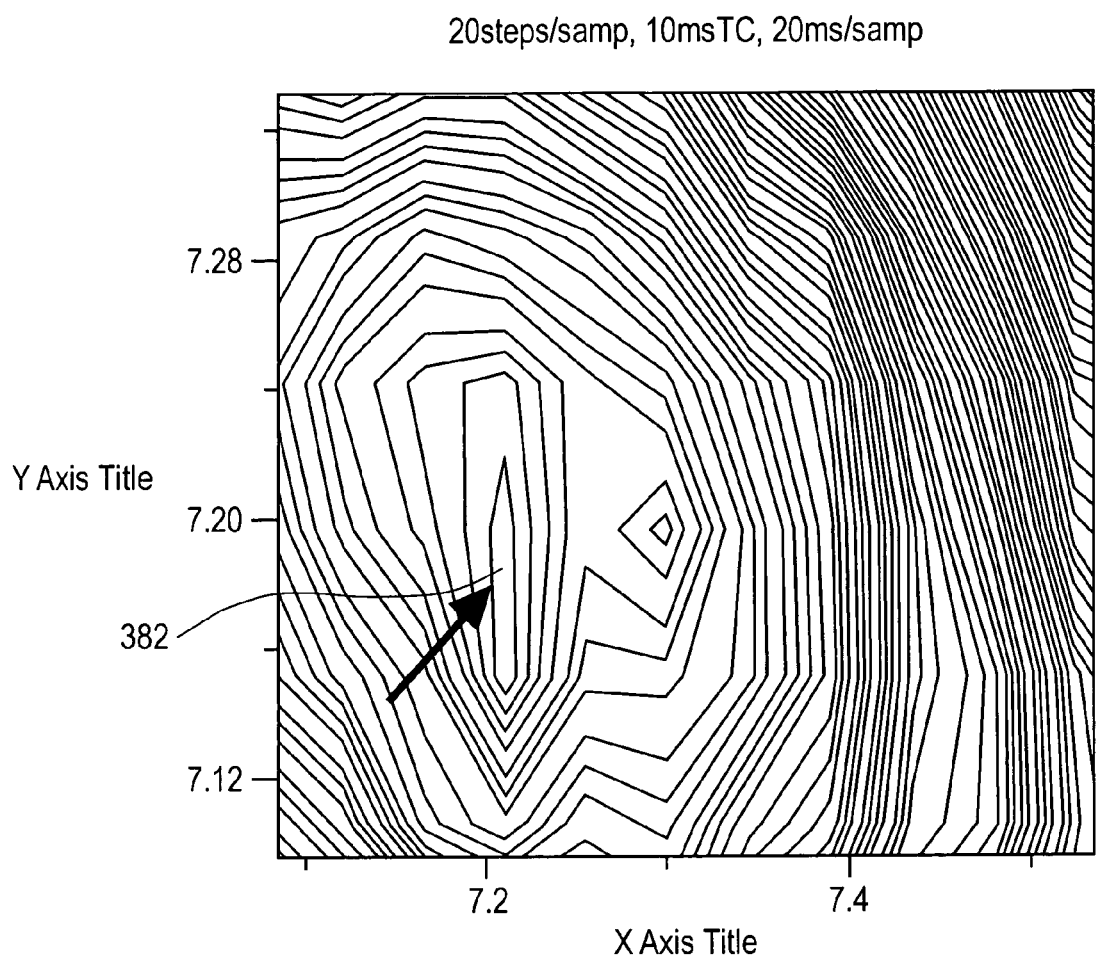
FIG. 16 is a simplified contour image of a portion of a circuit having a short.

FIG. 16 is a simplified contour image of a portion of a circuit (e.g., a microprocessor having a short 382 identified by a central contour line. The image may be generated by the material analysis system. The short is associated with a relatively large magnetic field associated with a relatively large current that flows into the short. The short might be associated with power up, power down or other circuit operation. The simplified image may be generated by cycling the VCC (e.g., applying a constant sine wave) on and off at 10 milliamps up to 50 milliamps at 5 kHz or the like.

Referring again FIGS. 14a and 14b, images 385a and 385b may be displayed on the display of computer 305 or computer 355 for analysis by a user. One or both of the images (or other images of the circuit boards) may be stored in database 350. The material analysis system may be configured to compare one or both of the images 385a and 385b with image data 387 for a known good circuit or known defective circuit. If an image included in the image data is determined by the material analysis system to substantially match image 385a, the system may determine that the PCB is operating as designed. Alternatively, if an image in the image data is determined by the material analysis system to substantially match image 385b, then the system may determine that PCB is flawed. The flaw may be indicated to the user via computer 305 or computer 355. Moreover, the location of a defect in two-dimensions or three-dimensions might be determined by the material analysis system and displayed on the display and/or for accumulation in the database. For example, in manufacturing test environments, image information for defects may be stored in a database so that common defects may be tallied and root causes of the defects identified so that defects introduced via manufacturing process may be reduced.

Figure 17:
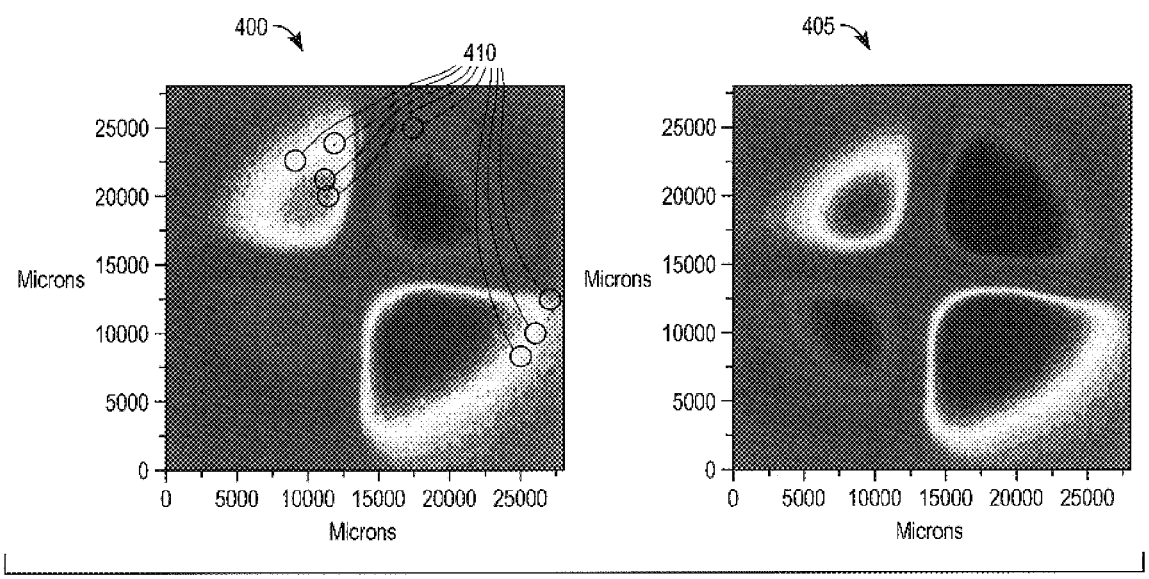
FIG. 17 includes a first simplified image of a "good" circuit and a second simplified image of a "defective" circuit according to one embodiment of the invention.

FIG. 17 includes a first simplified image 400 of a "good" circuit and a second simplified image 405 of a "defective" circuit according to one embodiment of the invention. The images are for the same type of circuit, such as a central processor unit (CPU). While the presently described example embodiment relates to a central processor unit, it should be understood that the presently described method may be applied to a variety of circuits and circuit types, such as, but not limited to memories, logic, ASICs, analog circuits, TTL, ECL, CMOS, bipolar and the like. Images 400 and 405 may be generated by one or more of the image formation methods described above. For example, images 400 and 405 may be snap shots of circuit operation for a single cycle of circuit operation, or by aggregating images (i.e., aggregating collect information for a number of operating cycles to generate an aggregated image). According to the exemplary embodiment of FIG. 17, image 400 and 405 may be generated by powering up and powering down the circuit a number of times at approximately 25 Hz or other frequency and aggregating data for one or more power up cycles of the circuit.

Either the first image 400 or the second image 405 may be an image previously generated and retrieved from database 350 for comparison with the other of the two images. Image 400 and 405 may be compared to determine whether the operated circuit is operating correctly or defectively. It may be known, for example, that a properly operating circuit includes a number of "hot spots" 410 in which current is configured to flow in the circuit during a "correct" power up sequence of the circuit. A hot spot refers to portion of a circuit in which current flow is detected via detection of the inducted magnetic fields associated with the current flow. A hot spot might be associated with a particular circuit element (e.g., a transistor, a capacitor, etc) or a number of circuit elements (e.g., a number of transistors, capacitors, etc.). As image 400 includes hot spots 410, the user or the material analysis system can determine that the operated circuit associated with image 400 operates properly during power up. And, as image 405 does include hot spots 410, the user or the material analysis system can determine that the operated circuit associated with this image does not operate properly during power up. It may be determined that the circuit associated with image 400 is operating properly or that the image associated with image 405 is not operating properly by comparing the images to image data 387 of a properly operating circuit. The nature of the defect of the circuit associated with image 405 may similarly be determined by comparing the image to image data 387 as this data includes information for a defectively operating circuit.

According to one embodiment, a circuit, such as a CPU, may fail at some time after power up (or "boot") or after some external event occurs. The material analysis system may collect magnetic field data for circuit activity during the time leading up to the failure and possibly afterwards.

A failure detection method according to one embodiment, may, for example, initially determine multiple problems in a circuit as evidenced by sufficiently unusual magnetic field signatures. For example, for a PCB that includes a number of bus-connected integrated circuits, unusual magnetic field signatures may be detected from one or more of the circuits. According to exemplary embodiment, a CPU on the PCB might be a prime suspect for defective operation. The magnetic fields generated by the CPU may be imaged and analyzed by the material analysis system for one or more inputs received from one or more input sources (logic circuits, memory circuits, other CPUs, etc on the PCB) that may be causing the problem in the CPU. For example, an interrupt input that has failed may cause the CPU to repeatedly execute the same small set of instructions (e.g., the interrupt service routine), creating a "repeating" magnetic signature. Clock chips, for example, on the PCB may be checked for proper activity, reset drivers compared and the like. The material analysis system may be configured to collect magnetic field information for numerous components on the PCB to determine the defective circuit by analyzing (e.g., comparing circuit operation to image data and or images stored in the database) the relation of the components in the circuit over time to determine the a particular sequence (e.g., a test sequence) that may be incorrect and determine the particular circuit that is the source of the defective operation of the CPU. This type of test system and analytical method is generally applicable to PCB that includes a plurality of circuits, a multichip module, or the like so that the material analysis system may be used for analyzing these various circuits without the use of hardware and/or software dedicated to each circuit.

Figure 18:
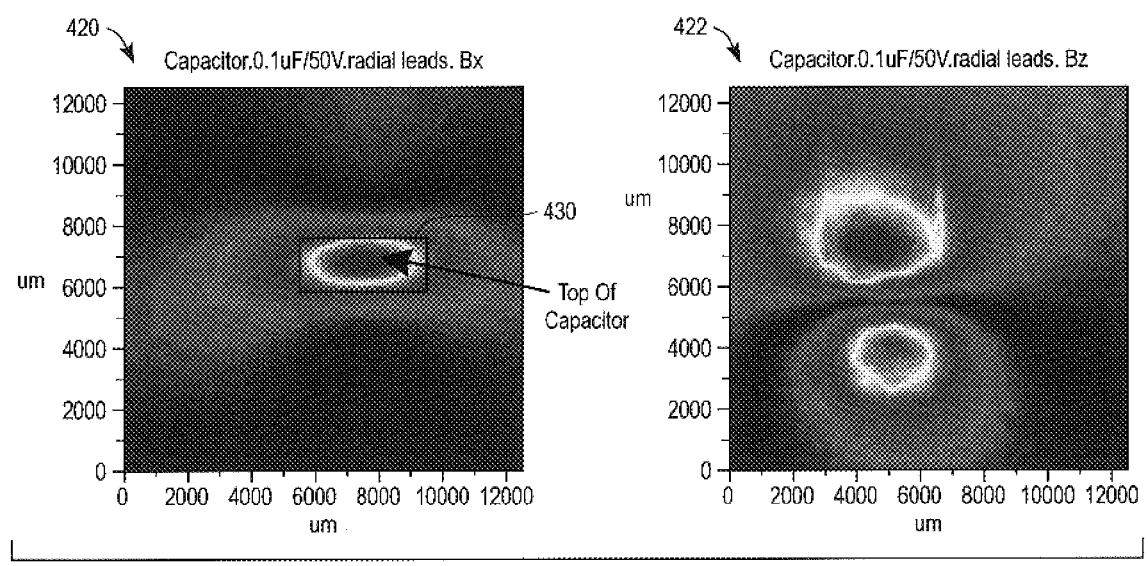
FIG. 18 is a simplified image of a top view and a cross-section view of a capacitor imaged by the material analysis system according to one embodiment of the present invention.
Figure 20A:
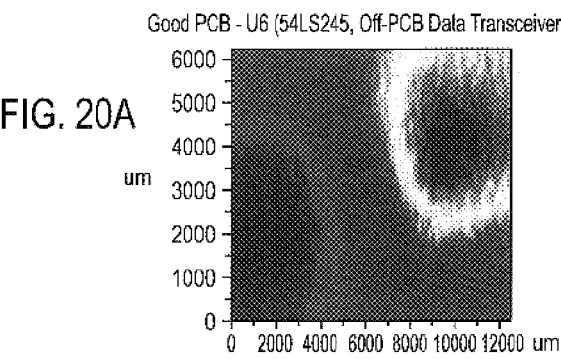
FIGS. 20A–20D are images of bi-directional transceiver that might be generated by the material analysis system from detected magnetic fields induced via operation of the transceivers.
Figure 20C:
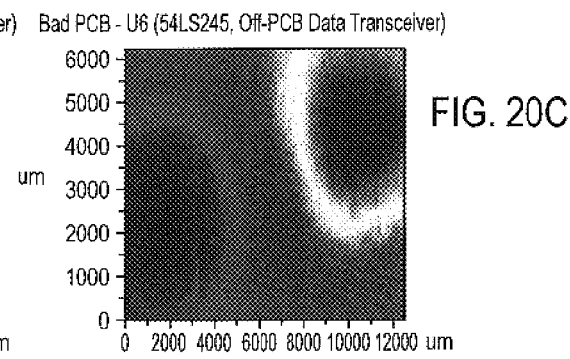
Figure 20B:
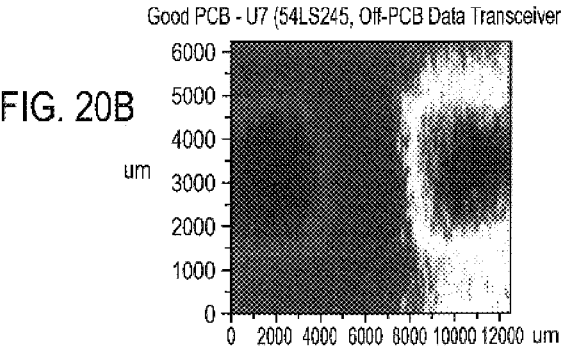
Figure 20D:
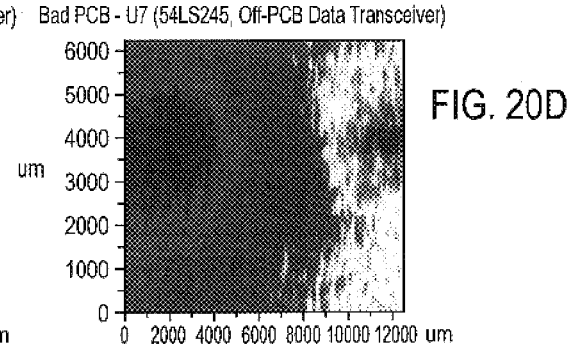

As described briefly above, the material analysis system is configured to generate two-dimensional and three-dimensional images of the circuit. The material analysis system is further configured to generate images of the circuit from different angles and at different cross sections. To enhance image generation for different angles and cross sections, the more sensitive (i.e., magnetic field sensitive) plane of the magnetic field sensors may be variously oriented (e.g., parallel, perpendicular, askew, etc.) with respect to the circuit's surface. FIG. 18 includes a top view 420 and a cross-section view 422 of a capacitor imaged by the material analysis system. The top plate of the capacitor is outlined by line 430 in images 420 and 422. The top view might be generated by orienting the more sensitive plane of the magnetic field sensors parallel to the top plate of the capacitor. The cross-section view might be generated by the material analysis system from magnetic field data collected with the magnetic field sensors parallel to the top plate of the capacitor or perpendicular to the top plate of the capacitor.

FIGS. 19A–19D include simplified images of address latches of the CPU that might be generated by the material analysis system. Address latches serve to "remember" each new address that the CPU specifies in fetching instructions. If the CPU is not providing addresses, the address latches will be idle. The magnetic field images in FIGS. 19A–19B and FIGS. 19C–19D show, respectively, the differences between properly operating addresses latches and defective address latches. FIGS. 19A and 19B indicate relatively high latch activity as the number of hot spots 450 is relatively large. In comparison, FIGS. 19C and 19D indicate relatively low latch activity from the relatively lower number of hot spots. The hot spots of FIGS. 19A and 19B are likely explained by the fact that the properly operating address latches generate relatively rapidly changing magnetic fields due to the internal switching of the digital components.

Figure 21:
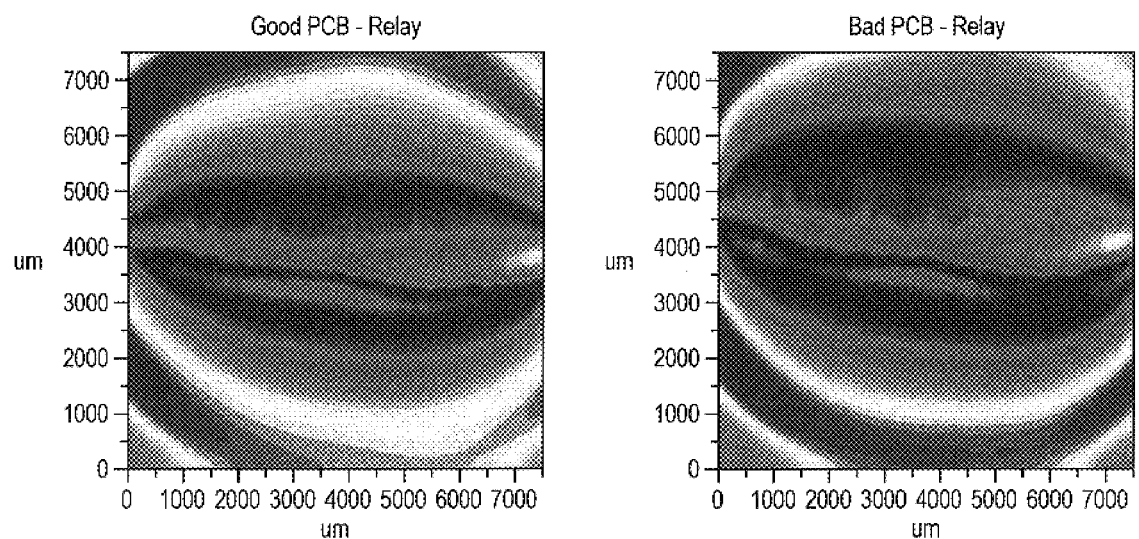
FIG. 21 includes two images of relays that may be generated from detected magnetic fields induced via operation of the relays.

FIGS. 20A–20D are images of bi-directional transceiver that might be generated by the material analysis system from detected magnetic fields induced via operation of the transceivers. FIG. 21 includes two images of relays that may similarly be generated from detected magnetic fields induced via operation of the relays.

Computer programs incorporating various features of the present invention may be encoded on various computer readable media for storage and/or transmission; suitable media include magnetic disk or tape, optical storage media such as CD or DVD, flash memory, and carrier signals adapted for transmission via wired, optical, and/or wireless networks conforming to a variety of protocols, including the Internet. Computer readable media encoded with the program code may be packaged with a compatible device or provided separately from other devices (e.g., via Internet download).

While the present invention has been described with reference to specific hardware and software components, those skilled in the art will appreciate that different combinations of hardware and/or software components may also be used, and that particular operations described as being implemented in hardware might also be implemented in software or vice versa.

Therefore, it is to be understood that the examples and embodiments described above are for illustrative purposes only and that various modifications or changes in light thereof will be suggested to persons skilled in the art and are to be included within the spirit and purview of this application and scope of the appended claims. For example, while image information stored in the database has been described as images collected for properly operating circuits and/or circuits with known defects, the images may be fabricated images that are modeled from a design specification or the like. Comparison of images generated by the material analysis system may be compared to the fabricated images for circuit testing, designs validation or the like. Therefore, the above description should not be taken as limiting the scope of the invention as defined by the claims.

What is claimed is:

1. A material analysis system configured to determine whether a circuit is functional or defective comprising:

a magnetic field generator configured to generate a first magnetic field that is configured to induce at least one eddy current in a conductive portion of the circuit, wherein the eddy current induces a second magnetic field;

a set of magnetic field sensors configured to detect the second magnetic field and generate a set of image information therefrom;

a database that includes circuit information for the circuit;

a computing device configured to receive the image information from the set of magnetic field sensors and retrieve the circuit information from the database, wherein the computing device is configured to compare the image information to the circuit information to determine whether the circuit is defective;

an electrical stimulation device configured to electrically stimulate the circuit, wherein a current associated with the electrical stimulus is configured to generate a third magnetic field in the conductive portion of the circuit, wherein the set of magnetic field sensors is configured to detect the third magnetic field and generate a second set of image information therefrom, and the computing device is configured to receive the second set of image information from the set of magnetic field sensors and compare the second set of image information to the circuit information to determine whether the circuit is defective.

2. The system of claim 1, wherein the set of magnetic field sensors includes a SQUID magnetometer, a set of Fluxgates, a set of Hall effect sensors, a set of magnetostrictive materials, and/or a set of magneto-resistive elements.

3. The system of claim 1, wherein the image information includes an image of the circuit and/or magnetic amplitude information for the second magnetic field.

4. The system of claim 3, wherein the circuit information includes a test image, a circuit layout, an image of a fabrication mask, a design specification, a design layout, and/or a conductor map.

5. The system of claim 4, wherein the test image includes an image of a non-defective circuit and/or a defective circuit having a known defect.

6. The system of claim 4, wherein the computing device includes a display and is configured to display the image on the display.

7. The system of claim 6, wherein the computing device is configured to display the test image on the display.

8. The system of claim 7, wherein the computing device is configured to superimpose the image and the test image on the display.

9. The system of claim 1, wherein the first mentioned set of image information includes a first image of the circuit, and the second set of image information includes a second image of the circuit.

10. The system of claim 9, wherein the computing device is configured to display on a computer display the first image and the second image.

11. The system of claim 9, wherein the first image and the second image are superimposed on the computer display.

12. The system of claim 9, wherein the computer is configured to scale the first image and/or the second image to substantially match at least one of a circuit layout, an image of a fabrication mask, a design layout, and/or a conductor map, and display the first image and/or the second image superimposed over at least one of the circuit layout, the image of the fabrication mask, the design layout, and/or the conductor map.

13. The system of claim 9, wherein the computer is configured to deconvolve the first image or the second image with the point spread function of the set of magnetic field sensors.

14. The system of claim 13, wherein the computer is configured to deconvolve the first image and/or the second image in the spatial domain and/or the Fourier domain.

15. The system of claim 14, further including a phase detector configured to detect a plurality of phase differences between the first magnetic field and the second magnetic field, wherein the plurality of phase differences are respectively associated with a plurality of conductive layers of the circuit disposed at a different circuit depths, and the computing system is configured to determine the depths from the phase differences.

16. The system of claim 1, wherein the computing device is configured to determine the heights of defects in the conductors based on three dimensional images generated of the magnetic fields.

17. The system of claim 1, wherein the computing device is configured to determine the horizontal positions of the defects based on the image information and horizontal position of the set of magnetic field sensors relative to the circuit.

18. A method for determining whether a circuit is defective comprising:

generating a first magnetic field that is configured to induce at least one eddy current in a conductive portion of the circuit, wherein the eddy current induces a second magnetic field;

detecting the second magnetic field;

generating a set of image information from the detected second magnetic field;

comparing the image information to predefined circuit information for the circuit;

electrically stimulating the circuit;

generating a third magnetic field based on the electrical stimulus in the conductive portion of the circuit;

detecting the third magnetic field;

generating a second set of image information from the detected third magnetic field;

comparing the second set of image information with the predetermined image information; and determining whether the circuit is defective based on the first and second comparing steps.

19. The method of claim 18, further comprising:

storing the predetermined circuit information in a database; and retrieving the predetermined circuit information from the database prior to the comparison step.

20. The system of claim 18, wherein:

the image information includes an image of the circuit, the predetermined circuit information includes a predetermined image for the circuit, and the comparing step includes comparing the image for the circuit and the predetermined image for the circuit.

21. The system of claim 20, wherein the predetermined image includes a predetermined image of a non-defective circuit and/or a defective circuit having a known defect.

22. The system of claim 20, further comprising displaying the image of the circuit and the predetermined image of the circuit.

23. The system of claim 22, wherein the step of displaying includes superimposing the image of the circuit and the predetermined image of the circuit.

24. The method of claim 18, further comprising displaying a first image associated with the first mention set of image information on a display superimposed with a second image associated with the second set of image information.

25. The method claim 24, further comprising scaling the first image and/or the second image to substantially match at least one of a circuit layout, an image of a fabrication mask, a design layout, and/or a conductor map.

26. The method of claim 25, further comprising displaying the first image and/or the second image superimposed over at least one of the circuit layout, the image of the fabrication mask, the design layout, and/or the conductor map.

27. The system of claim 24, further comprising deconvolving the first image or the second image with the point spread function of the set of magnetic field sensors to substantially remove information associated with the set of magnetic field sensors from the first image or the second image.

* * * * *